United States Patent
Miyazawa

(10) Patent No.: US 11,020,065 B2
(45) Date of Patent: Jun. 1, 2021

(54) CONTROL DEVICE FOR CONTROLLING TOMOSYNTHESIS IMAGING, IMAGING APPARATUS, IMAGING SYSTEM, CONTROL METHOD, AND PROGRAM FOR CAUSING COMPUTER TO EXECUTE THE CONTROL METHOD

(71) Applicant: CANON KABUSHIKI KAISHA, Tokyo (JP)

(72) Inventor: Nobu Miyazawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 794 days.

(21) Appl. No.: 14/898,878

(22) PCT Filed: Jun. 18, 2014

(86) PCT No.: PCT/JP2014/066162
§ 371 (c)(1),
(2) Date: Dec. 16, 2015

(87) PCT Pub. No.: WO2014/203933
PCT Pub. Date: Dec. 24, 2014

(65) Prior Publication Data
US 2016/0135760 A1      May 19, 2016

(30) Foreign Application Priority Data
Jun. 18, 2013   (JP) ............................. JP2013-127978

(51) Int. Cl.
A61B 6/02      (2006.01)
A61B 6/00      (2006.01)

(52) U.S. Cl.
CPC ............ *A61B 6/025* (2013.01); *A61B 6/4452* (2013.01); *A61B 6/463* (2013.01); *A61B 6/465* (2013.01);
(Continued)

(58) Field of Classification Search
CPC ....... A61B 6/025; A61B 6/4452; A61B 6/463; A61B 6/465; A61B 6/467; A61B 6/5205;
(Continued)

(56) References Cited

U.S. PATENT DOCUMENTS 6,016,438 A  *  1/2000  Wakayama ............ G06T 19/00
                                                    324/307
6,178,220 B1 *  1/2001  Freundlich ............ G06T 11/003
                                                    378/15
(Continued)

FOREIGN PATENT DOCUMENTS

CN    102525501 A    7/2012
JP    63-102748 A    5/1988
(Continued)

*Primary Examiner* — Dani Fox
*Assistant Examiner* — Soorena Kefayati
(74) *Attorney, Agent, or Firm* — Canon U.S.A., Inc., IP Division

(57) ABSTRACT

In tomosynthesis imaging for obtaining a tomographic image from a plurality of projected images, at least generation or display of a two-dimensional tomographic image along a plane intersecting a detection surface of an X-ray detection unit is controlled in accordance with information on X-ray irradiation directions in which the projected images are respectively captured.

24 Claims, 16 Drawing Sheets

(52) U.S. Cl.
CPC ............ *A61B 6/467* (2013.01); *A61B 6/5205* (2013.01); *A61B 6/5223* (2013.01); *A61B 6/54* (2013.01); *A61B 6/545* (2013.01); *A61B 6/547* (2013.01)

(58) Field of Classification Search
CPC ......... A61B 6/5223; A61B 6/54; A61B 6/545; A61B 6/547; G06T 11/003; G06T 2207/30068; G06T 2207/10121; G06T 2219/028
See application file for complete search history.

(56) References Cited

U.S. PATENT DOCUMENTS

| | | | | |
|---|---|---|---|---|
| 6,236,708 | B1 * | 5/2001 | Lin | A61B 6/025 378/22 |
| 8,913,715 | B2 * | 12/2014 | Iordache | G06T 11/206 378/25 |
| 9,113,796 | B2 * | 8/2015 | Engel | G06T 15/08 |
| 2003/0142119 | A1 * | 7/2003 | Akagi | A61B 6/4283 345/698 |
| 2003/0194121 | A1 * | 10/2003 | Eberhard | G06T 7/0012 382/132 |
| 2004/0101092 | A1 * | 5/2004 | Matsumoto | A61B 6/4233 378/22 |
| 2005/0105678 | A1 * | 5/2005 | Nakashima | A61B 6/4085 378/4 |
| 2005/0113681 | A1 * | 5/2005 | DeFreitas | A61B 6/025 600/426 |
| 2005/0171430 | A1 * | 8/2005 | Zhang | A61B 8/13 600/437 |
| 2006/0008049 | A1 * | 1/2006 | Matsumoto | H04N 5/32 378/19 |
| 2006/0033679 | A1 * | 2/2006 | Gunji | G06T 11/008 345/33 |
| 2006/0085407 | A1 * | 4/2006 | Kaminaga | G16H 30/40 |
| 2006/0291717 | A1 * | 12/2006 | Mussack | A61B 6/463 382/154 |
| 2007/0109294 | A1 * | 5/2007 | Gotman | A61B 6/467 345/418 |
| 2007/0242797 | A1 * | 10/2007 | Stewart | A61B 6/502 378/16 |
| 2008/0008401 | A1 * | 1/2008 | Zhu | A61B 5/05 382/294 |
| 2009/0008581 | A1 * | 1/2009 | Fujiwara | G01N 23/046 250/580 |
| 2009/0147909 | A1 * | 6/2009 | Yoda | A61B 6/032 378/4 |
| 2010/0027859 | A1 * | 2/2010 | Heinlein | A61B 6/463 382/128 |
| 2010/0195789 | A1 * | 8/2010 | Kanagawa | G01N 23/044 378/11 |
| 2010/0290592 | A1 * | 11/2010 | Yamada | A61B 6/00 378/114 |
| 2011/0058724 | A1 * | 3/2011 | Claus | A61B 6/025 382/132 |
| 2012/0099776 | A1 * | 4/2012 | Maeda | A61B 6/032 382/131 |
| 2012/0189091 | A1 * | 7/2012 | Jerebko | A61B 6/5223 378/4 |
| 2012/0321034 | A1 * | 12/2012 | Nakayama | G06T 7/0002 378/4 |
| 2013/0121556 | A1 * | 5/2013 | Matsumoto | A61B 6/50 382/132 |
| 2013/0208852 | A1 * | 8/2013 | Koishi | A61B 6/548 378/19 |
| 2014/0086470 | A1 * | 3/2014 | Mukumoto | A61B 6/466 382/131 |
| 2014/0093030 | A1 * | 4/2014 | Mukumoto | A61B 6/032 378/4 |
| 2014/0138553 | A1 * | 5/2014 | Ogawa | G01T 1/17 250/393 |
| 2014/0350381 | A1 * | 11/2014 | Kim | A61B 5/7282 600/411 |
| 2015/0084959 | A1 * | 3/2015 | Nitta | G06T 11/60 345/427 |
| 2015/0157287 | A1 * | 6/2015 | Iordache | A61B 6/025 378/20 |
| 2015/0165235 | A1 * | 6/2015 | Fujisawa | A61B 6/5288 382/131 |
| 2015/0230770 | A1 * | 8/2015 | Heinlein | A61B 6/54 600/425 |
| 2016/0073974 | A1 * | 3/2016 | Saito | A61B 6/06 378/98.2 |
| 2016/0073986 | A1 * | 3/2016 | Saito | A61B 6/032 378/4 |

FOREIGN PATENT DOCUMENTS

| | | |
|---|---|---|
| JP | 4-109935 A | 4/1992 |
| JP | 10-272128 A | 10/1998 |
| JP | 2000-046760 A | 2/2000 |
| JP | 2004-173857 A | 6/2004 |
| JP | 2005-300438 A | 10/2005 |
| JP | 2009-011646 A | 1/2009 |
| JP | 2009-153928 A | 7/2009 |
| JP | 2010-172527 A | 8/2010 |
| JP | 2012-152436 A | 8/2012 |
| WO | 2014/203936 A1 | 12/2014 |

* cited by examiner

CONTROL DEVICE FOR CONTROLLING TOMOSYNTHESIS IMAGING, IMAGING APPARATUS, IMAGING SYSTEM, CONTROL METHOD, AND PROGRAM FOR CAUSING COMPUTER TO EXECUTE THE CONTROL METHOD

TECHNICAL FIELD

The present disclosure relates to a control device for controlling tomosynthesis imaging for capturing projected images of a plurality of frames and obtaining a tomosynthesis image from the plurality of projected images, an imaging apparatus, an imaging system, a control method, and a program for causing a computer to execute the control method.

BACKGROUND ART

In tomosynthesis imaging, an X-ray generation apparatus irradiates a person being examined with X-rays at different angles while being moved and an X-ray detector detects X-rays transmitted through the object, thereby allowing continuous capture of projected images of a plurality of frames having different imaging angles. The captured projected images of the plurality of frames are shifted so that the preset center positions thereof coincide with each other to make corresponding pixels overlap each other, thereby executing the reconstruction of a tomosynthesis image that is a tomographic image of a certain cross section of the person being examined (PTL 1). In tomosynthesis imaging, because of the limitations on the irradiation angle, a tomographic image along a detection surface of an X-ray detector, for example, a coronal image, is often used.

In addition, CT (Computed Tomography) has a function of generating and displaying images of a plurality of cross sections, such as coronal, sagittal, axial, and oblique images (PTL 2).

CITATION LIST

Patent Literature

PTL 1: Japanese Patent Laid-Open No. 2000-46760
PTL 2: Japanese Patent Laid-Open No. 2005-300438

SUMMARY OF INVENTION

Technical Problem

In tomosynthesis imaging, however, the limitations on the irradiation angle or an insufficient number of projected images because of factors such as interrupted imaging may have a large effect on the quality of, in particular, a tomographic image along the detection surface of the X-ray detector (in the example described above, an image of a cross section intersecting a coronal image).

Solution to Problem

Accordingly, a control device for controlling tomosynthesis imaging according to an embodiment of the present invention is a control device for controlling tomosynthesis imaging for obtaining a tomographic image from a plurality of projected images captured by irradiating an object with X-rays from a plurality of different angles by using an X-ray generation unit and an X-ray detection unit. The control device includes image processing means for generating a two-dimensional tomographic image along a plane intersecting a detection surface of the X-ray detection unit on the basis of the captured projected images, and display control means for controlling display of the two-dimensional tomographic image in accordance with irradiation directions of the X-ray generation unit with respect to the detector with which the plurality of projected images are respectively captured.

Advantageous Effects of Invention

In the manner described above, an apparatus capable of generating a two-dimensional tomographic image along a plane intersecting a detection surface of an X-ray detection unit on the basis of projected images obtained through tomosynthesis imaging limits the display of the two-dimensional tomographic image, which may largely affect image quality, leading to less likelihood of false diagnosis caused by the display of a tomographic image having low quality.

DESCRIPTION OF EMBODIMENTS

The configuration and operation of an X-ray imaging system according to an embodiment of the present invention will be described hereinafter with reference to FIGS. 1 to 16.

Figure 1:
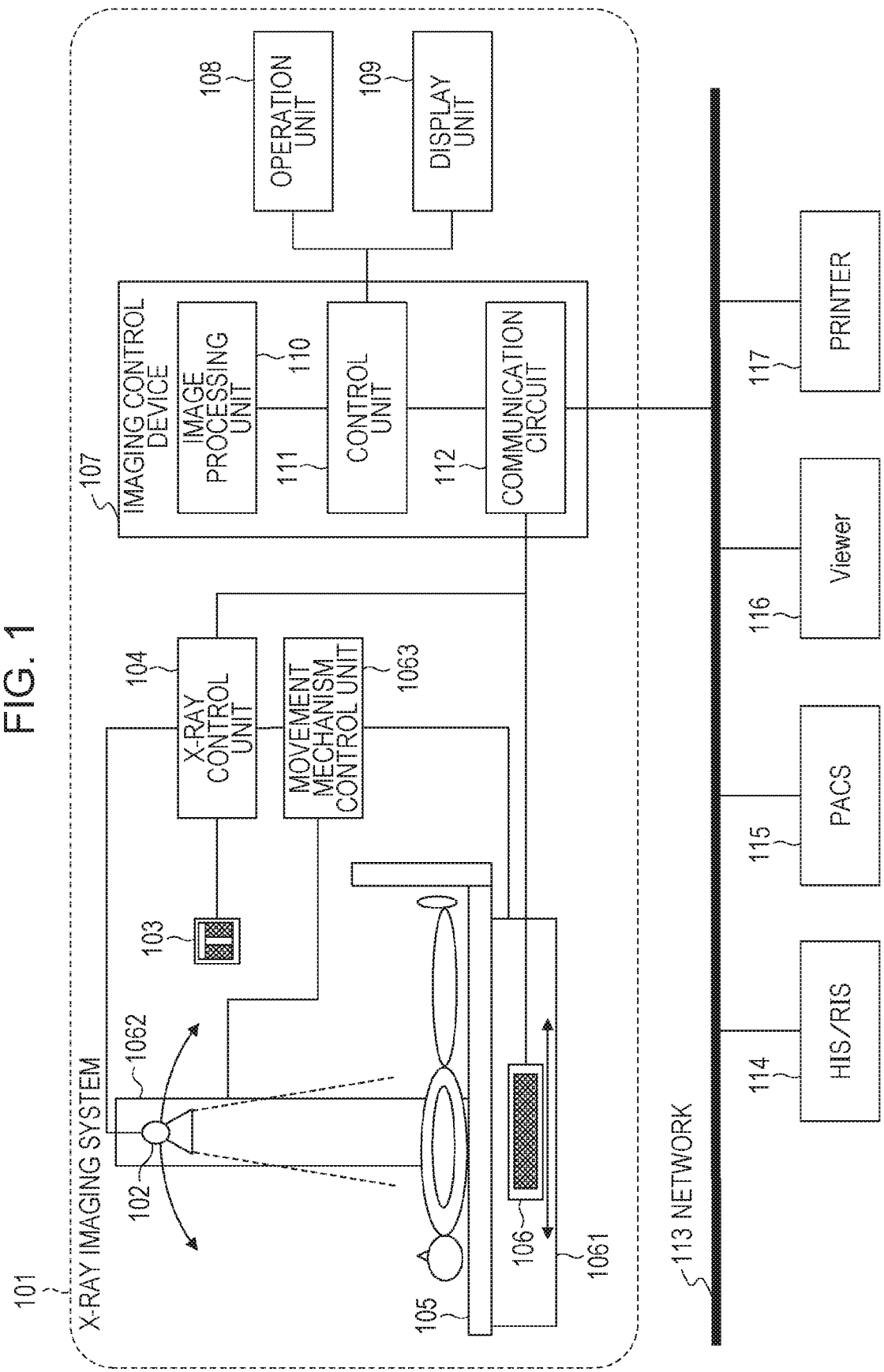
FIG. 1 is a configuration diagram of an X-ray imaging system according to an embodiment of the present invention.

FIG. 1 illustrates the configuration of an X-ray imaging system according to an embodiment of the present invention. An X-ray imaging system 101 includes an X-ray generation unit 102, a movement mechanism 1061, a column 1062, an X-ray irradiation switch 103, an X-ray control unit 104, an imaging table 105, an X-ray detector 106, an imaging control device 107, an operation unit 108, and a display unit 109. The X-ray detector 106 and the imaging control device 107 collectively serve as an X-ray imaging apparatus, in particular. The X-ray generation unit 102 and the X-ray control unit 104 collectively serve as an X-ray generation apparatus, in particular. The movement mechanism 1061, the column 1062, and a movement mechanism control unit 1063 collectively serve as an imaging system holding apparatus. The term imaging system, as used herein, is used to include the X-ray generation apparatus and the X-ray imaging apparatus, namely, the X-ray generation unit 102 and the X-ray detector 106. The X-ray generation apparatus and the imaging system holding unit may be collectively referred to as an X-ray generation apparatus.

The X-ray generation unit 102 performs X-ray irradiation. Further, the X-ray generation unit 102 transmits imaging execution conditions such as tube voltage and tube current and position information such as an imaging angle and an X-ray source moving distance to the X-ray control unit 104 in accordance with X-ray irradiation. Further, the X-ray generation unit 102 receives default imaging conditions and default position information from the X-ray control unit 104, and performs an imaging preparation process.

The movement mechanism 1061 is capable of linearly moving the X-ray detector 106 in the direction of the axis of the body of the object, for example. The column 1062 includes a movement mechanism that movably supports the X-ray generation unit 102, and is capable of moving the X-ray generation unit 102 along an arc in the direction of the axis of the body of the object.

The movement mechanism control unit 1063 controls the movement of the movement mechanism 1061 of the X-ray detector and the column 1062. The movement mechanism control unit 1063 is capable of moving the movement mechanism 1061 and the column 1062 in synchronization with each other. Here, the movement mechanism 1061 and the column 1062 are moved in synchronization with each other, the X-ray generation unit 102 is moved in a first direction, and the X-ray detector 106 is moved in a direction opposite to the first direction, thereby providing an execution of tomosynthesis imaging for obtaining projected images from a plurality of directions.

Further, the movement mechanism control unit 1063 is connected to the X-ray control unit 104. The movement mechanism control unit 1063 receives information on the timing of X-ray irradiation, and outputs position information on the X-ray generation unit 102 and the X-ray detector 106 at this timing to the X-ray control unit 104. For example, in the case of intermittent emission of pulsed X-rays, position information on the X-ray generation unit 102 and the X-ray detector 106 at the start of emission of the pulsed X-rays, at the end of the emission, or at a certain time during the emission is output.

The X-ray irradiation switch 103 transmits an irradiation start notification and an irradiation end notification to the X-ray control unit 104. When pressed by an operator, the X-ray irradiation switch 103 transmits an irradiation start notification. When released by the operator, the X-ray irradiation switch 103 transmits an irradiation end notification. When the X-ray irradiation switch 103 is being pressed, a sequence of projected images is captured while the X-ray generation unit 102 and the X-ray detector 106 are moved. During the capture of a sequence of projected images, for example, The X-ray generation unit 102 performs X-ray irradiation while being moved over a range from minus 30 degrees to plus 30 degrees. In this case, if the pressing of the X-ray irradiation switch 103 is stopped in the middle of the range at the time when an angle of plus 10 degrees is reached, the capture of projected images is interrupted. Note that a 0-degree position is established when the column 1062 extends in the vertical direction.

The X-ray control unit 104 is connected to the X-ray generation unit 102, the X-ray irradiation switch 103, and the imaging control device 107. The X-ray control unit 104 controls the start and end of X-ray irradiation, and transmits imaging execution conditions and position information. Further, the X-ray control unit 104 receives imaging conditions and position information from the imaging control device 107, and notifies the X-ray generation unit 102 of the imaging conditions and the position information.

The imaging table 105 is a support on which an object is placed. The movement mechanism 1061 of the X-ray detector, which moves the X-ray detector 106 in a direction along the top of the table, is provided immediately below the top.

The X-ray detector 106 includes an X-ray sensor having a plurality of photoelectric conversion elements arranged in a matrix. The X-ray detector 106 detects X-rays transmitted through the object, and converts the X-rays into X-ray image data. A discrete two-dimensional planar array of the plurality of photoelectric conversion elements defines an X-ray detection region and an X-ray detection surface. The X-ray detection surface extends in a direction along a surface of the X-ray detector 106, and is desirably substantially parallel to an upper surface. The X-ray detector 106 is arranged substantially in parallel to the top of the imaging table. In addition, the X-ray detector moves substantially in parallel to the top, and therefore the X-ray detector 106 moves along the X-ray detection surface. Here, "substantially" means that complete parallelism is not required for imaging and, for example, an error of about several degrees is tolerable.

The X-ray detector 106 is further connected to the imaging control device 107, and transmits the X-ray image data to the imaging control device 107 together with imaging execution information such as the scan area and the binning size and position information such as the X-ray detector moving distance. Further, the X-ray detector 106 receives default position information from the imaging control device 107, and performs an imaging preparation process. The transmission of the X-ray image data and the imaging execution and position information is performed by using wired communication via a cable connected to the imaging control device 107 or by using wireless communication. The imaging control device 107 may be configured to receive position information on the X-ray detector 106 from the X-ray control unit 104 via the movement mechanism control unit 1063.

The imaging control device 107 is a control device that totally controls the X-ray imaging system. The imaging control device 107 controls X-ray imaging with a combination of the X-ray control unit 104 and the X-ray detector 106, a reconstruction process using the X-ray image data, image processing such as tone conversion processing to be performed on the X-ray image data, an execution of an examination including X-ray imaging, input and output to and from the operation unit 108 and the display unit 109, transmission and reception to and from an external device via a network 113, and other operations. The imaging control device 107 is constituted by an image processing unit 110, a control unit 111, and a communication circuit 112.

The imaging control device 107 executes a method for controlling tomosynthesis imaging for obtaining a tomographic image from projected images obtained by irradiating an object with X-rays from a plurality of different angles by using an X-ray generation unit and an X-ray detection unit.

The imaging control device 107 is connected to the X-ray control unit 104 and the X-ray detector 106. The imaging control device 107 acquires projected images obtained through X-ray imaging and position information on the X-ray detector 106 and the X-ray generation unit 102 when the projected images are obtained, and reconstructs a tomosynthesis image. The image obtained by reconstruction is displayed on the display unit 109.

Additionally, the imaging control device 107 is connected to an HIS/RIS 114, a PACS 115, a viewer 116, and a printer 117 via the network 113. The HIS/RIS 114 is a hospital/radiology information management system for managing information in the radiology department, such as patient information and examination request information. The PACS 115 is an image management server whose main purpose is to save images. The viewer 116 is connected to the PACS 115, and a high-definition monitor is mainly used for visual inspection and detailed post-processing of an image obtained by imaging using the X-ray imaging system 101, and for diagnostic operations. The printer 117 prints and outputs the X-ray image data or tomosynthesis image data.

The image processing unit 110 performs image processing, such as tone conversion processing and noise reduction processing, on the received X-ray image data. Further, the image processing unit 110 performs a reconstruction process using the X-ray image data and the position information to reconstruct a tomosynthesis image. An image reconstructed from projected images obtained through tomosynthesis imaging is referred to as a tomosynthesis image in particular. A tomosynthesis image according to one embodiment is a representation of three-dimensional volume data based on a plurality of projected images.

The control unit 111 performs control for the execution of an examination and the execution of imaging, or saves/reads information on the execution of a suspended examination or a completed examination or X-ray image data. Further, the control unit 111 determines the situation in which interruption of imaging is occurring on the basis of the notified position information, and determines the availability of the execution of reconstruction and the availability of the display of an oblique cross section. Further, the control unit 111 calculates valid frames of a tomosynthesis image on the basis of the notified position information.

The communication circuit 112 transmits a variety of driving conditions such as an accumulation period of time, a binning condition, and a frame rate, in addition to an X-ray irradiation preparation request and an X-ray irradiation preparation cancellation request, to the X-ray control unit 104 and the X-ray detector 106 via a communication I/F. Further, the communication circuit 112 receives X-ray image data, imaging execution information, and position information from the X-ray control unit 104 and the X-ray detector 106. Further, the communication circuit 112 receives examination request information, transmits examination execution information, and outputs the X-ray image data or tomosynthesis image data via the network 113.

The operation unit 108 is an input interface that accepts an operation performed by an operator. The input interface of the operation unit 108 may be any interface having input capabilities, such as a keyboard, a mouse, or a multi-touch monitor. The operation unit 108 transmits input information to the imaging control device 107 in accordance with the operation. Further, the operation unit 108 receives a request from the imaging control device 107, and switches the display of the input interface.

The display unit 109 is an output interface on which a user interface of control software for X-ray imaging is displayed. The display unit 109 may be any interface having display capabilities, such as a separate monitor or a monitor incorporated in an X-ray imaging apparatus. A plurality of monitors on which captured images are displayed may be connected to a single imaging control device 107, and a captured image and a previous image may be displayed as previews on different monitors. In this case, the display unit 109 judges on which monitor and which image is displayed in accordance with a notification from the imaging control device 107.

The image processing unit 110 further generates a two-dimensional tomographic image from the volume data, if necessary. Examples of the generated two-dimensional tomographic image include a tomographic image (first two-dimensional tomographic image) in the direction along the detection surface. Referring to the configuration of the imaging system illustrated in FIG. 1, this tomographic image corresponds to a coronal image of the object. A two-dimensional tomographic image in the direction along the detection surface (referred to as a first two-dimensional tomographic image) is often used since an obtained tomographic image can at least have sufficient image quality, which depends on the limitations on the irradiation angle in tomosynthesis imaging.

In addition, the image processing unit 110 is also capable of generating a two-dimensional tomographic image intersecting the detection surface (second two-dimensional tomographic image). For example, the image processing unit 110 is capable of generating a so-called oblique image that is a tomographic image having a certain inclination to the direction of the axis of the body of the object, that is, the movement direction of the X-ray generation unit 102 and the X-ray detector 106. Needless to say, it is possible to generate any other two-dimensional tomographic image intersecting the detection surface. For example, referring to the imaging system illustrated in FIG. 1, sagittal images or axial images can be generated. In the case of tomosynthesis imaging in which the X-ray generation unit 102 and the X-ray detector 106 are moved along the axis of the body of the object, it can be conceived in terms of image quality that an oblique image is generated whereas no sagittal image or axial image is generated. In the case of tomosynthesis imaging in which the X-ray generation unit 102 and the X-ray detector 106 are two-dimensionally moved along the top of the imaging table 105, a sagittal image or an axial image may be generated.

In another embodiment, a set of two-dimensional tomographic images along, more desirably, parallel to, the detection surface of the X-ray detector 106 may be directly reconstructed from a sequence of projected images, and may be handled as a tomosynthesis image. In this case, a process for directly reconstructing, for example, each of oblique, sagittal, and axial images from projected images is executed.

The communication circuit 112 transmits driving conditions for the X-ray detector 106 to the X-ray detector 106, and receives from the X-ray detector 106 a sequence of projected images to be used for the reconstruction process based on projected images described above. Accordingly, the imaging control device 107 can obtain projected images to be used for a reconstruction process.

In addition, the communication circuit 112 receives from the X-ray control unit 104 position information on the X-ray generation unit 102 and the X-ray detector 106 at the timings when the respective projected images are captured. In this regard, the communication circuit 112 functions as a unit for acquiring projected images and position information. Based on the sequence of projected images and the position information, the image processing unit 110 performs a reconstruction process. The position information includes, for example, information on the direction in which the X-ray generation unit 102 performs X-ray irradiation to the X-ray detector 106.

Here, the desired tomographic image may not be obtained due to the interruption of the imaging or the limitations on the movement mechanism 1061 or the movement mechanism of the column 1062 or depending on conditions such as the imaging interval for projected images or the setting of the irradiation angle or the range of the irradiation direction of the X-ray generation unit 102.

Accordingly, the control unit 111 performs display control to impose a limitation on a second two-dimensional tomographic image to be displayed, by using the information on the irradiation direction of the X-ray generation unit 102 within the position information obtained from the communication circuit 112. For example, projected images have been obtained in the irradiation direction from −30 degrees to +10 degrees. In this case, a limitation is imposed such that an oblique image having an intersection angle up to ±10 degrees to the detection surface of the X-ray detector 106 or the top of the imaging table 105 is displayed, whereas an oblique image having an intersection angle larger than +10 degrees or an intersection angle smaller than −10 degrees is not displayed. It is a matter of course that an oblique image having an intersection angle up to ±5 degrees may be a target to be displayed. Further, an oblique image may be displayed with an intersection angle in the range from −30° to +10°. In another example, projected images have been obtained with irradiation angles in the range from −20 degrees to +20 degrees. In this case, a limitation is imposed such that an oblique image having an intersection angle up to ±20 degrees to the detection surface of the X-ray detector 106 or the top of the imaging table 105 is displayed, whereas an oblique image having an intersection angle larger than +20 degrees or an intersection angle smaller than −20 degrees is not displayed.

In the way described above, a process for specifying the range of the display target on the basis of the range of the irradiation direction, causing a second two-dimensional tomographic image within the specified range of the display target, and removing a second two-dimensional tomographic image outside the range from the display target is executed. This enables a two-dimensional tomographic image of a guaranteed sufficient quality to be displayed, and can reduce the probability of false diagnosis.

In another example, in the case of irradiation over a range from −30 degrees to 30 degrees, the display of oblique images is prohibited if only projected images up to −5 degrees have been obtained. In still another example, in the case of similar irradiation conditions, the display of oblique images is also uniformly prohibited if only projected images over a range from −30 degrees to 10 degrees are successfully obtained due to circumstances such as interruption of the imaging. In the manner described above, if it is determined that projected images satisfying the desired irradiation conditions are not successfully obtained, a uniform limitation on the display of oblique images can ensure higher image quality.

In still another example, if the irradiation interval for projected images is 0.5 degrees, oblique images are also controlled not to be displayed at intervals less than 0.5 degrees, and, if the irradiation interval is 0.1 degrees, oblique images are also controlled not to be displayed at intervals less than 0.1 degrees. In the manner described above, a limitation on the display interval of oblique images by using information on X-ray irradiation directions for the respective projected images can ensure the quality of the oblique images to be displayed.

In addition, such generation and display of coronal images or oblique images are performed within a modality, in particular, by the imaging control device 107 that controls tomosynthesis imaging. Accordingly, whether or not tomosynthesis imaging is appropriate can be checked before transmission to the PACS 115 and the like, enabling an improvement in the efficiency of medical diagnosis.

Figure 2:
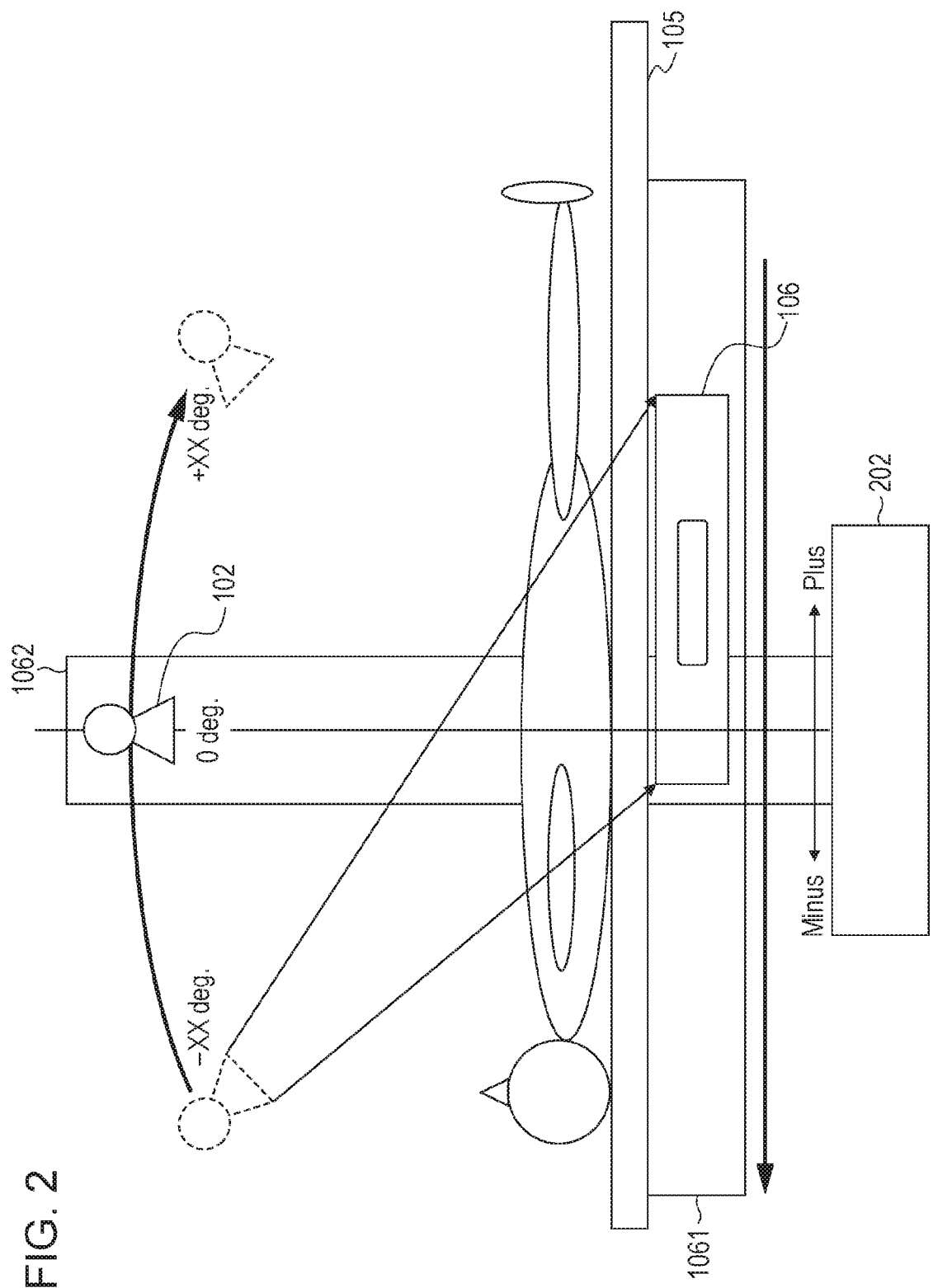
FIG. 2 is a system configuration diagram of tomosynthesis imaging according to the embodiment of the present invention.

Here, a system configuration related to tomosynthesis imaging is illustrated using FIG. 2. The X-ray generation unit 102 is fixed to the column 1062 which is inclinable. During the collection of projected image data, the X-ray generation unit 102 and the X-ray detector 106 move in horizontally opposite directions, with respect to, as a center, a position at which the imaging table 105 and the column 1062 are perpendicular to each other before the start of irradiation, by a preset distance in a direction (horizontal direction) along the imaging table 105 and the detection surface. In this case, the irradiation range of the X-ray generation unit 102 is set so as to be included in the detection region of the X-ray detector 106. Along with the start of irradiation, the X-ray generation unit 102 and the X-ray detector 106 collect projected image data on which the reconstruction process is based and acquires position information while moving toward the center. The tomosynthesis image described above is generated based on the projected image data obtained by imaging in the way described above.

The imaging control device 107 or the X-ray control unit 104 sets the range of the irradiation direction or the irradiation interval of the X-ray generation unit 102. In this embodiment, the column 1062 is configured to allow the X-ray generation unit 102 to move on an arc, where the position at which the column 1062 is vertical is defined as a 0-degree position and a θ direction is plotted in the left-to-right direction in FIG. 2. In addition to this, setting information indicating plus minus θ degrees is input to the movement mechanism control unit 1063 from the imaging control device 107 or the X-ray control unit 104, and the column 1062 causes the X-ray generation unit 102 to move so that the initial position before the imaging is minus θ degrees. When the X-ray generation unit 102 is at a position of θ° with respect to the upright direction of the column 1062 (the vertical direction), θ° is referred to as an irradiation angle. Furthermore, a direction connecting the focal point of the X-ray generation unit 102 and the center position of the X-ray detector 106 at this time is referred to as an X-ray irradiation direction. The angle defined by the X-ray irradiation direction with respect to the vertical direction is 0° in the condition where an isocenter for tomosynthesis imaging is fixed. Thus, in the following exemplary embodiment, the irradiation angle and the irradiation direction are used with similar meanings.

In FIG. 2, the X-ray generation unit 102 moves from left to right. In accordance with this setting information, the movement mechanism 1061 allows the X-ray detector 106 to move. The range of the irradiation direction is not limited to the definition described above, and, for example, a position of −90 degrees in the example described above may be used as a reference. As an alternative, the range of the irradiation direction of the X-ray generation unit 102 may be set using a parameter other than the angle. For example, as in FIG. 2, the distance over which the center position of the column 1062 or the X-ray generation unit 102 is displaced from the state where the column 1062 is upright may be used as setting information. Setting information is converted into the movement mechanism 1061 or the column 1062 or a control value by the X-ray control unit 104 or the movement mechanism control unit 1063, and is output to a driving mechanism for these components, such as a motor, so that the driving mechanism allows the X-ray generation unit 102 and the X-ray detector 106 to move.

The imaging interval is a parameter indicating an interval at which projected images are captured, and has a value defined by the interval of the irradiation angle, for example. Alternatively, the imaging interval can be defined by a displacement of the X-ray generation unit 102 in the horizontal direction with respect to the position at which the column 1062 is upright. The imaging interval is not necessarily an equal interval, and is decided on as necessary. For example, in the case of imaging with an irradiation angle of ±30 degrees, the imaging interval is decided on by setting the number of imaging sessions. In the case of tomosynthesis imaging in the step-and-shoot mode, the movement mechanism control unit 1063 causes the movement mechanism 1061 and the column 1062 to move by a control amount corresponding to the interval of the irradiation angle, and the X-ray control unit 104 instructs the X-ray generation unit 102 to emit X-rays at the timing when the movements are stopped. After the X-ray irradiation is completed, the movement mechanism control unit 1063 again causes the movement mechanism 1061 and the column 1062 to move by a control amount defined by the parameter of the imaging interval. In the case of tomosynthesis imaging in the continuous mode, X-rays are emitted during the movement. The movement mechanism control unit 1063 continuously monitors the positions, and the X-ray control unit 104 starts X-ray irradiation at the timing when an X-ray irradiation position (imaging position) defined by the imaging interval is reached.

Figure 3:
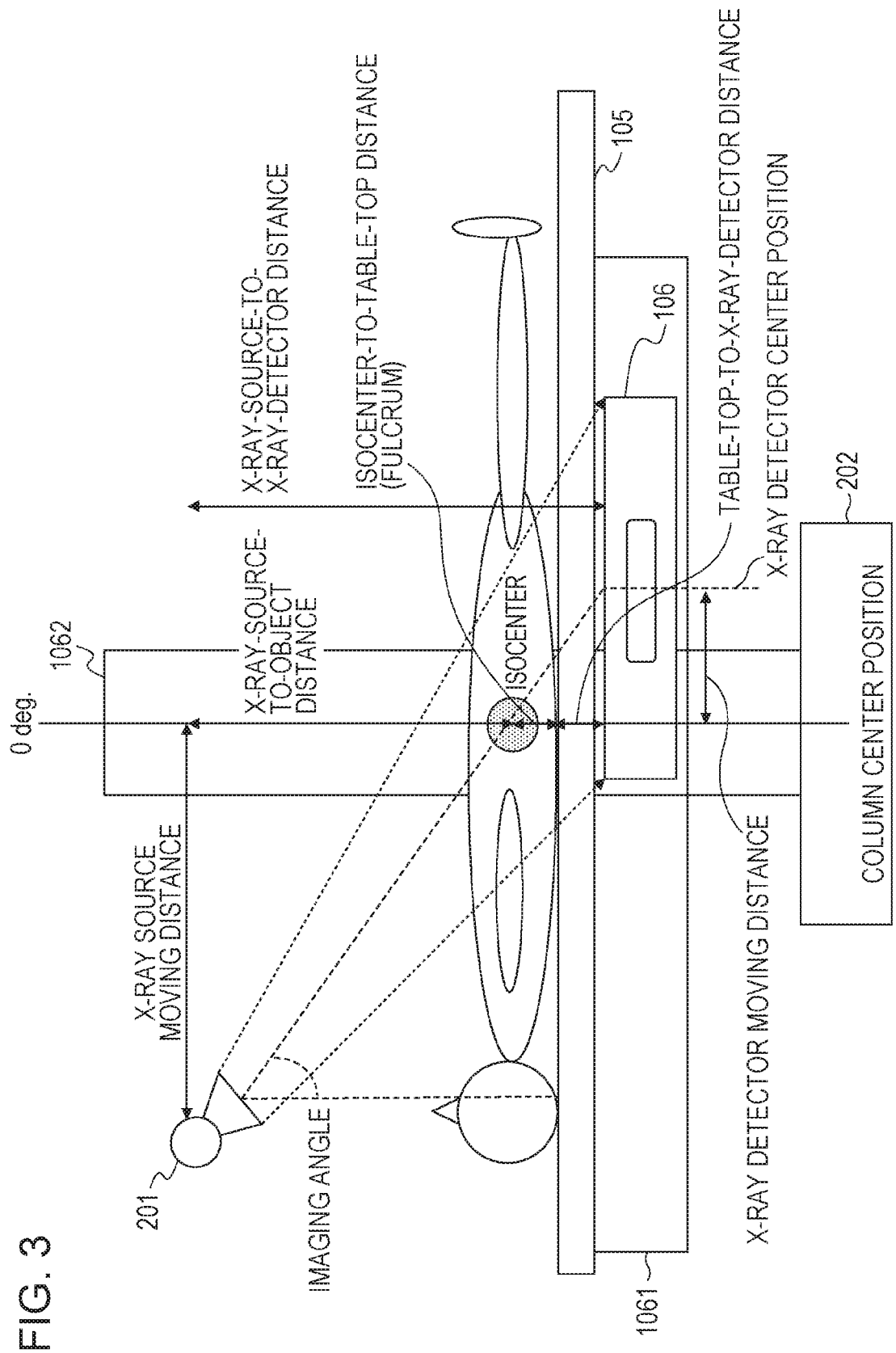
FIG. 3 is a diagram illustrating position information acquired during tomosynthesis imaging.

FIG. 3 illustrates the details of the position information obtained during the collection of projected image data. As a method for moving the X-ray generation unit 102, either a method in which the column 1062 horizontally moves or a method in which the column 1062 is inclined in its portion in contact with a foundation 202 may be used.

Here, the details of the position information are illustrated using FIG. 3. Here, the angle at which the imaging table 105, the X-ray detector 106, and the column 1062 to which an X-ray source 201 is fixed are perpendicular is defined as 0°. (I do not have a good explanation for this; the absolute value of the angle increases like ±1, 2, . . . as inclination increases in opposite directions from 0°). Further, a position at which the X-ray detector 106, the X-ray source 201, and the position of the isocenter are aligned in series with a position perpendicular to the imaging table 105 is defined as a center position at which the moving distance is 0. (The absolute value of the moving distance increases like ±1, 2, . . . in accordance with movements in opposite directions from the center position). The isocenter is in a tomographic position at which the clearest image is generated among a plurality of frames of a tomosynthesis image created by reconstruction. The respective moving distances of the X-ray source 201, the X-ray detector 106, and the imaging table 105 on which the object is placed are controlled so that the isocenter is always located on a straight line connecting the focal point position of the X-ray source 201 and the detection region center position of the X-ray detector 106 during the capture of projected images. The isocenter-to-table-top distance (hereinafter, referred to the fulcrum) is the distance from the isocenter at the center position to the topmost of the imaging table 105. A specific value is used for each imaging session. The fulcrum is set as one of the default imaging conditions included in imaging technique information. In addition, a temporary change to the settings or a change to the default settings can be made by input to the operation unit 108 during the execution of an examination. The X-ray control unit 104 controls the operation of the X-ray generation unit 102 by referring to the fulcrum received from the imaging control device 107. Thereafter, at the completion of irradiation for projected images, the X-ray control unit 104 receives the input of fulcrum as a piece of position information, and transmits the fulcrum to the imaging control device 107. The fulcrum is used for the reconstruction process based on the FBP (Filtered Back Projection) algorithm and the shift-and-add algorithm. The fulcrum is also used for the calculation of the X-ray-source-to-object distance. The imaging angle is the inclination of the X-ray source 201 when the center position is 0°. A maximum imaging angle is set as one of the default imaging conditions included in imaging technique information. In addition, a temporary change to the settings or a change to the default settings can be made by input to the operation unit 108 during the execution of an examination. In a single imaging session, the inclination is successively changed from the maximum imaging angle in the negative direction to the maximum imaging angle in the positive direction through the center position. The positive and negative directions in which the inclination is changed may be reversed. As the imaging angle, an imaging angle obtained when image data is read is acquired for each of a plurality of consecutive X-ray image frames of projected images. At the completion of irradiation for projected images, the X-ray control unit 104 receives the input of the imaging angle as a piece of position information, and transmits the imaging angle to the imaging control device 107. An imaging angle pitch that is changed for each read of image data is decided on by dividing the amount by which the angle is changed in a single imaging session by the number of frames scheduled to be captured. The imaging angle is used for the reconstruction process based on the FBP (Filtered Back Projection) algorithm and the shift-and-add algorithm. The imaging angle is also used for the determination of an imaging state by an imaging interruption determination unit 401. In addition, the imaging angle is further used for limiting the designation of the angle during the display of a reconstruction oblique cross section. The X-ray source moving distance is a distance through which the X-ray source 201 moves in a direction parallel to the imaging table 105 with respect to the center position. The X-ray source 201 moves to the right or left from the center position in synchronization with the X-ray detector 106, and is inclined at an angle that allows the isocenter to be located on a straight line connecting the focal point position of the X-ray source 201 and the detection region center position of the X-ray detector 106 to meet the imaging angle corresponding to the setting. Accordingly, the X-ray source moving distance is decided on in synchronization with the setting of the imaging angle. As the X-ray source moving distance, an X-ray source moving distance obtained when image data is read is acquired for each of a plurality of consecutive X-ray image frames of projected images. At the completion of irradiation for projected images, the X-ray control unit 104 receives the input of an X-ray source moving distance for each X-ray image frame as a piece of position information, and transmits the X-ray source moving distance to the imaging control device 107. The X-ray source moving distance is used for the reconstruction process based on the FBP (Filtered Back Projection) algorithm and the shift-and-add algorithm. The X-ray detector moving distance is a distance through which the X-ray detector 106 moves in a direction parallel to the imaging table 105 with respect to the center position. The X-ray detector 106 moves to the right or left from the center position in a direction opposite to that of the X-ray source 201 in synchronization with the X-ray source 201, and moves so that the isocenter is located on a straight line connecting the focal point position of the X-ray source 201 and the detection region center position of the X-ray detector 106 to meet the imaging angle corresponding to the setting. Accordingly, similarly to the X-ray source moving distance, the X-ray detector moving distance is also decided on in synchronization with the setting of the imaging angle. As the X-ray detector moving distance, an X-ray detector moving distance obtained when image data is read is acquired for each of a plurality of consecutive X-ray image frames of projected images. At the completion of irradiation for projected images, the X-ray control unit 104 receives the input of an X-ray detector moving distance for each X-ray image frame as a piece of position information, and transmits the X-ray detector moving distance to the imaging control device 107. The X-ray detector moving distance is used for the reconstruction process based on the FBP (Filtered Back Projection) algorithm and the shift-and-add algorithm. An X-ray-source-to-X-ray-detector distance is a distance from the X-ray source 201 at the center position to the topmost of the X-ray detector 106. The X-ray-source-to-X-ray-detector distance has a specific value for each imaging apparatus. The X-ray-source-to-X-ray-detector distance is used for the calculation of the X-ray-source-to-object distance. A table-top-to-X-ray-detector distance is a distance from the topmost of the imaging table 105 at the center position to the topmost of the X-ray detector 106. The table-top-to-X-ray-detector distance has a specific value for each imaging apparatus. The table-top-to-X-ray-detector distance is used for the calculation of an X-ray-source-to-object distance. The X-ray-source-to-object distance is a distance from the X-ray source 201 at the center position to the object with respect to the isocenter. The X-ray-source-to-object distance has a specific value for each imaging session depending on the fulcrum set for each imaging session. More specifically, the X-ray-source-to-object distance is calculated by an imaging control unit 405 in accordance with the equation below using the X-ray-source-to-X-ray-detector distance, fulcrum, and table-top-to-X-ray-detector distance included in the position information received by the imaging control device 107 at the completion of irradiation for projected images.

X-ray-source-object distance=X-ray-source-to-X-ray-detector distance−(fulcrum+table-top-to-X-ray-detector distance)

The X-ray-source-object distance is used for the reconstruction process based on algorithms such as the FBP (Filtered Back Projection) algorithm and the shift-and-add algorithm.

The parameters described above are used as position information on the X-ray generation unit 102 and the X-ray detector 106. Among the pieces of position information, the isocenter position, the table-top-to-X-ray-detector distance, and the fulcrum have common values for the imaging system or in a single imaging session, whereas the other pieces of position information are different for the capture of each projected image. Accordingly, a set of pieces of position information common for a single imaging session and position information different for each projected image is output from the X-ray control unit 104 to the imaging control device 107 via the movement mechanism control unit 1063.

Figure 4:
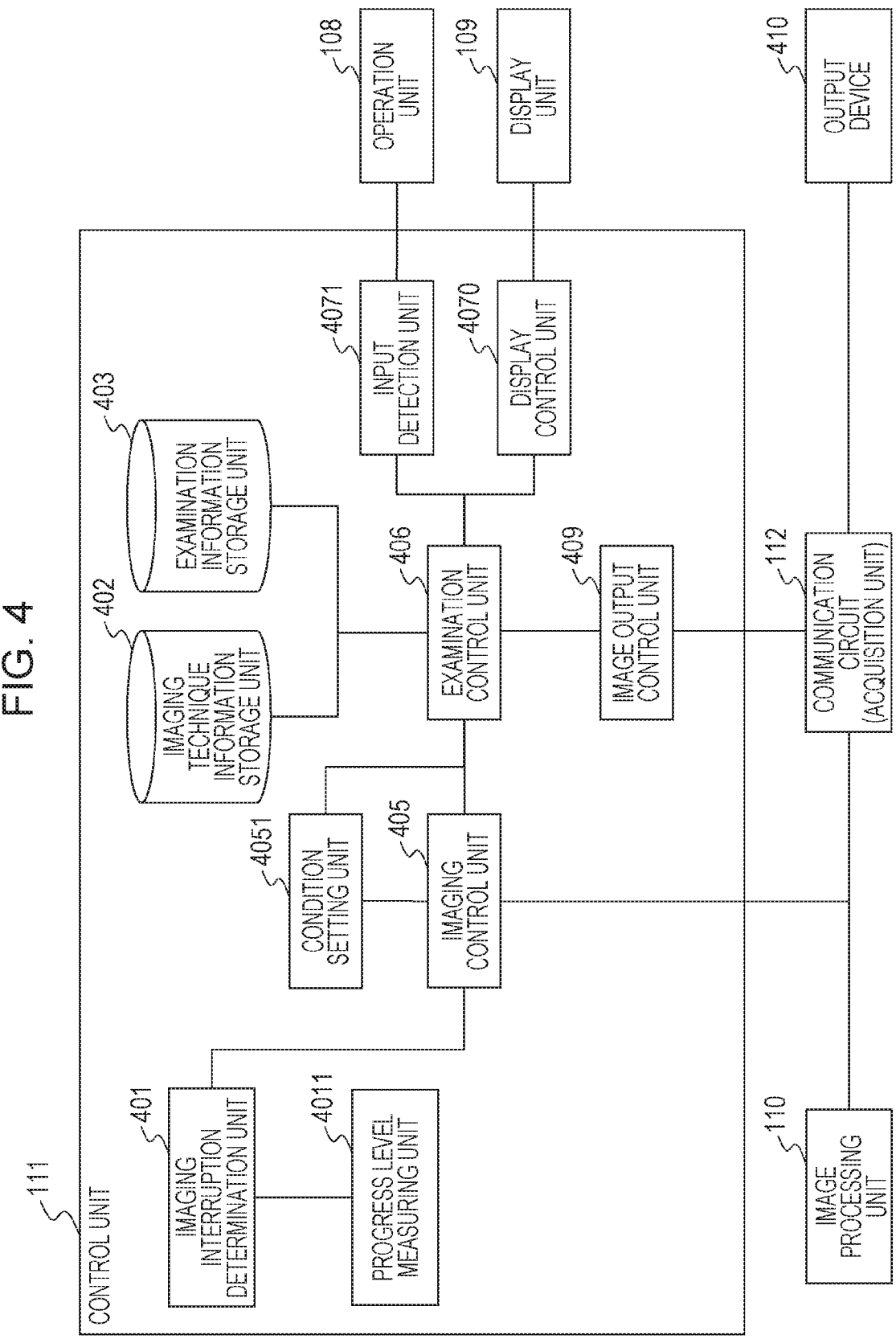
FIG. 4 is a configuration diagram of an imaging control unit according to the embodiment of the present invention.

FIG. 4 illustrates a detailed configuration of the control unit 111 related to the X-ray imaging system 101 in the present invention. The control unit 111 includes the imaging interruption determination unit 401, an imaging technique information storage unit 402, an examination information storage unit 403, an imaging control unit 405, a condition setting unit 4051, an examination control unit 406, a display control unit 4070, an input detection unit 4071, an image output control unit 409, and a progress level measuring unit 4011.

The imaging technique information storage unit 402 saves, updates, deletes, and searches for imaging technique information. The imaging technique information illustrated here includes items that can be set for each imaging technique and that cover from the execution of imaging to post-processing and image output settings, such as information for identifying an imaging technique such as the part to be imaged and the imaging direction, imaging conditions, image processing parameters, reconstruction parameters, storage transfer settings, and printing settings. The imaging technique information storage unit 402 is constituted by a database. The examination information storage unit 403 registers, updates, deletes, and searches for examination information of examination information. The examination information storage unit 403 is constituted by a database.

The imaging control unit 405 transmits and receives data of imaging availability, imaging execution conditions, and position information to and from the X-ray generation unit 102 and the X-ray detector 106 via the communication circuit 112. Further, the imaging control unit 405 performs control of the overall flow of a single X-ray imaging session and the overall flow of the execution of a reconstruction process, such as control for the execution of a reconstruction process and the storage of X-ray image data.

The condition setting unit 4051 sets an imaging condition in accordance with, for example, an operation input from the operation unit 108. The condition setting unit 4051 is a setting unit that extracts imaging conditions from the imaging technique information obtained from the imaging technique information storage unit 402 and that transmits the imaging conditions as imaging parameters to the respective units such as the imaging control unit 405, the image processing unit 110, the X-ray detector 106, the X-ray generation unit 102, and the movement mechanism control unit 1063. The term imaging parameters, as used herein, is used to include, for example, the number of projected images captured, the imaging interval for projected images, information on a range of X-ray irradiation positions (±θ), the number of coronal image first secondary tomographic images (coronal images) created, the creation pitch, other image processing parameters, and drive parameters for the X-ray detector 106.

The examination control unit 406 performs control of the overall flow of the execution of an examination, such as control of the update/registration of patient information, examination-scheduled-to-be-conducted information, and imaging technique information, control of screen transitions, storage of tomosynthesis image data, and a process for adding a tomosynthesis image. The term examination refers to a concept that encompasses a plurality of units of imaging, and common information is processed for a transition between imaging sessions and a plurality of imaging sessions included in one unit of examination.

The input detection unit 407 accepts and interprets an operation input from the operation unit 108. The display control unit 4070 performs the overall display control of the display unit 109 in response to output instructions notified by the examination control unit 406, such as a screen transition. For example, the display control unit 4070 performs display control of a projected image or a tomosynthesis image, a process for changing the display of a GUI (Graphical User Interface) in accordance with the operation input to the operation unit 108, and so forth.

The image output control unit 409 determines image output availability of an image included in the received examination information, and instructs the communication circuit 112 to output the image to an output device 410. The output device 410 corresponds to, for example, the PACS 115, the viewer 116, or the printer 117.

The imaging interruption determination unit 401 determines whether or not the imaging has been interrupted, by using the position information notified from the X-ray control unit 104. If the imaging is interrupted, position information not corresponding to a predetermined range of irradiation positions is obtained or the number of projected images is insufficient to meet a specified amount. Accordingly, the imaging interruption determination unit receives, as input, information on a preset number of projected images captured, information on the range of irradiation positions, position information obtained as a result of imaging, information on projected images, and other information, and determines whether or not the tomosynthesis imaging has been interrupted.

An example of the interruption determination method is as follows. In a case where the number of projected images captured has been set by the condition setting unit 4051, if the number of projected images obtained through the communication circuit 112 is less than that value, the imaging interruption determination unit 401 determines that the imaging has been interrupted. If both numbers match, the imaging interruption determination unit 401 determines that the imaging has been completed.

In another example, it is determined that the imaging has been interrupted if the number of elements of position information included in the set of pieces of position information obtained from the X-ray control unit 104 is smaller than a predetermined number of captured images, and it is determined that the imaging has been completed if the number of elements is equal to the number of captured images. If the number of elements of position information is larger than the number of captured images, it can be determined that an error has occurred. Alternatively, if at least one of the number of pieces of position information and the number of projected images is smaller than a prescribed number of captured images, it is determined that the imaging has been interrupted. If both numbers match the number of captured images, it is determined that the imaging has been completed without interruption. Such an example is also provided.

In another example, in a case where the range of irradiation positions is set to ±θ, it is determined that the imaging has been interrupted if the position information obtained through the communication circuit 112 ranges from −θ to +θ' (<θ), and it is determined that the imaging has been completed if data in the range from −θ to +θ has been obtained. In this case, the actually set range does not necessarily exactly match a range of position information acquired in actuality. Thus, for example, any digits in the difference after the decimal place are ignored and it is determined that an interruption has occurred.

Alternatively, the X-ray control unit 104 may be configured to output notifications of the start, interruption, and completion of imaging, and the output may be received by the communication circuit 112 and interpreted by the interruption determination unit 401 to determine that an interruption has occurred.

Alternatively, there is also considered a case where the pieces of position information described above are not used directly for determination. For example, during imaging, the communication circuit 112 regularly receives the progress of capturing projected images from the X-ray control device 104. If the X-ray control device 104 notifies the imaging control device 107 of the completion of the imaging before the progress reaches 100%, it is determined that an interruption has occurred. If there is a notification indicating that the progress has reached 100%, it is determined that the imaging has been completed without interruption. The progress is obtained in the X-ray control device 104 by, for example, dividing the number of times irradiation has been provided by a specified number of times of irradiation. Instead of the progress, the value of the number of times imaging has been performed (the number of times of irradiation) can be directly handled as information indicating the degree of progress.

Alternatively, such a degree of progress can be obtained within the control unit 111. In such an embodiment, the control unit 111 includes the progress level measuring unit 4011. The progress level measuring unit 4011 measures a level of progress of imaging by using setting information, such as the number of projected images captured and the information on the range of irradiation positions, and execution information, such as the number of projected images that have been captured and the set of pieces of position information. After the completion of the imaging, the progress level measuring unit 4011 identifies a degree of progress indicating a degree to which the capture of projected images has been completed, or a level of progress of imaging, by using information such as the set of pieces of position information.

The display control unit 4070 limits the display of oblique images or second two-dimensional tomographic images by using the information on the degree of progress of the imaging. For example, the display of oblique images is limited in accordance with the degree of progress in such a manner that, if it is determined that the imaging has been interrupted when the degree of progress is 60%, oblique images having intersection angles up to 5 degrees to the detection surface are displayed, and oblique images having intersection angles up to 15 degrees are displayed if an interruption has occurred when the degree of progress is 80%. The relationship between the degree of progress and the degree of limitation of display can be experimentally determined.

In addition, for example, the display control unit 4070 imposes a limitation so that no two-dimensional tomographic image (second two-dimensional tomographic image) intersecting the detection surface is displayed if the imaging interruption determination unit 401 determines that an interruption has occurred and if the degree of progress is greater than or equal to 50% and less than 100%. On the other hand, since the degree of progress is greater than or equal to 50%, the embodiment in FIG. 2 described above allows projected image data obtained by irradiation from the respective positions in the range of at least −θ° to 0° to have been obtained. Thus, a two-dimensional tomographic image (coronal image) along the detection surface is displayed because the quality can be guaranteed. This threshold value may be set as desired by the display control unit 4070 or may be experimentally determined in accordance with the progress and information on irradiation positions. If the degree of progress is less than 50%, the display of both a first tomographic image and a second tomographic image is limited. In this case, the imaging control unit 405 additionally performs control to prohibit the reconstruction process for a tomosynthesis image, which is performed by the image processing unit 110, to lessen the processing load. In this case, furthermore, the image output control unit 409 handles imaging data of the relevant projected image group as reject data, and limits the output of such data to the output device 410, which can prevent unwanted image data from being output.

Figure 5:
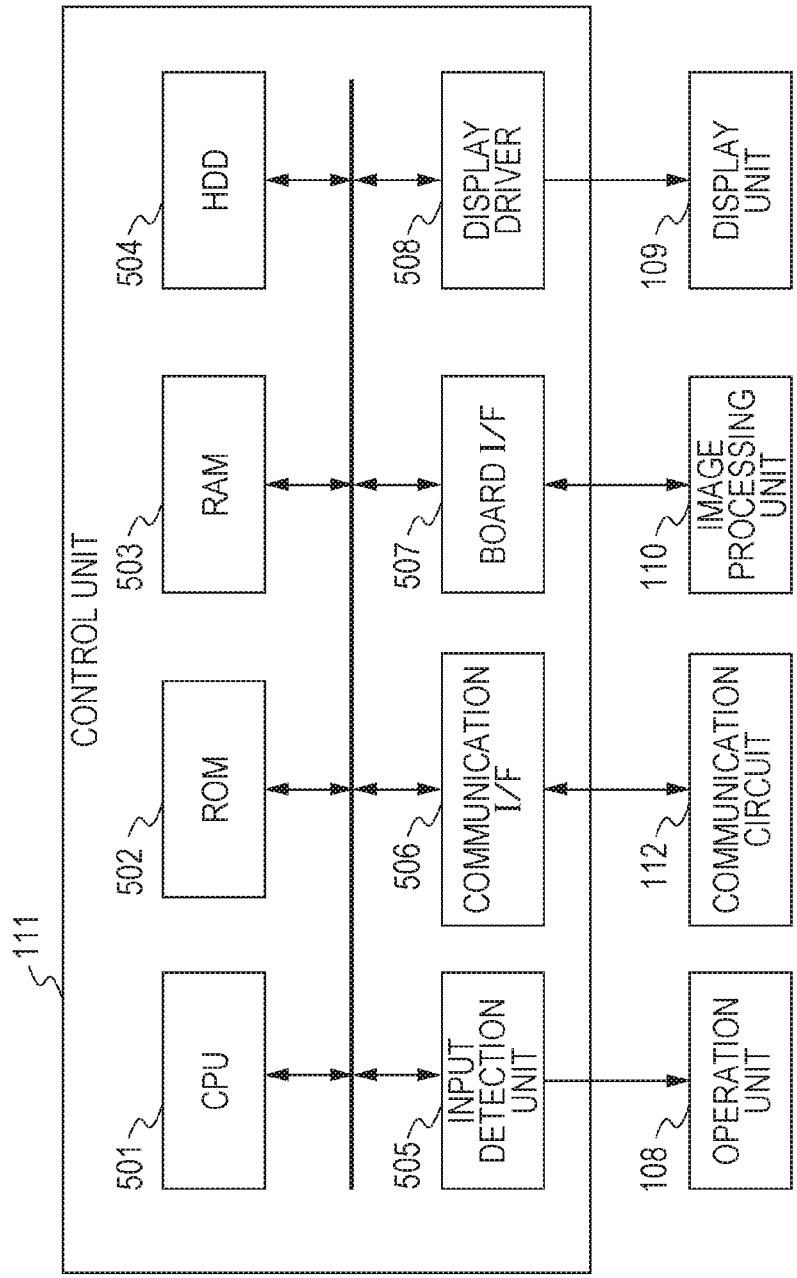
FIG. 5 is a hardware configuration diagram of the imaging control unit according to the embodiment of the present invention.

The hardware example configuration of the imaging control device according to the embodiment will be described with reference to FIG. 5. The control unit 111 includes a CPU 501, a ROM 502, a RAM 503, an HDD 504, an input detection unit 505, a communication I/F 506, a graphics board 507, and a display driver 508. These components are connected to one another via a bus such as a data bus. The CPU 501 is configured to perform the overall control of the control unit 111, and executes an instruction program stored in the ROM 502 to execute control. The program is executed by the CPU 501 to cause the control unit 111 to exert the functions of the imaging interruption determination unit 401, the progress level measuring unit 4011, the imaging technique information storage unit 402, the examination information storage unit 403, the imaging control unit 405, the condition setting unit 4051, the examination control unit 406, the display control unit 4070, the input detection unit 4071, and the image output control unit 409. Further, the program is a program for executing processes illustrated in FIG. 6, FIG. 7, and FIG. 13 described below.

Further, the CPU 501 performs input/output control for the display unit 109 via the display driver 508, and input/output control for the operation unit 108 via the input detection unit 505. The RAM 503 is configured to reserve a working storage area when the CPU performs control in accordance with an instruction program. The HDD 504 is an auxiliary storage device that saves various kinds of data such as X-ray image data. The communication I/F 506 is a communication interface constituting the communication circuit 112, and transmits and receives data between the control unit 111 and each of the X-ray control unit 104, the X-ray detector 106, and the network 113. The graphics board 507 is configured to constitute the image processing unit 110, and performs image processing and a reconstruction process using a GPU.

Subsequently, an example of the flow from the start to the end of a typical tomosynthesis imaging examination in the present invention is illustrated using FIG. 6.

In step S601, patient information is created prior to the start of the examination. The patient information illustrated here includes all the pieces of information for identifying a patient, such as the patient's name, patient ID, age, date of birth, gender, height, weight, and pregnancy state.

In step S601, the display unit 109 displays a patient information input screen 801. When an instruction for confirming the patient information is given, the operation unit 108 transmits a patient information confirmation notification including the patient information to the input detection unit 4071. Upon receipt of the patient information confirmation notification, the input detection unit 4071 transmits the patient information confirmation notification to the examination control unit 406. Upon receipt of the patient information confirmation notification, the examination control unit 406 newly generates examination-scheduled-to-be-conducted information. The examination-scheduled-to-be-conducted information illustrated here includes the patient information described above, examination information including all the items for identifying an examination, such as examination ID and examination date and time, and imaging technique information including all the pieces of information for identifying an imaging technique, such as the part to be imaged. Then, the examination control unit 406 inputs the patient information included in the patient information confirmation notification to the examination-scheduled-to-be-conducted information. Thereafter, the examination control unit 406 transmits a notification of a request to obtain all the registered imaging technique information to the imaging technique information storage unit 402. Upon receipt of the notification of the request to obtain all the imaging technique information, the imaging technique information storage unit 402 acquires all the registered imaging technique information, and transmits the acquired imaging technique information to the examination control unit 406. Upon receipt of the imaging technique information, the examination control unit 406 transmits an imaging technique selection screen transition notification together with the imaging technique information to the display control unit 4070. Upon receipt of the imaging technique selection screen transition notification, the display control unit 4070 transmits the imaging technique selection screen transition notification to the display unit 109 for display. Upon receipt of the imaging technique selection screen transition notification, the display unit 109 displays an imaging technique selection screen 901. The display unit 109 displays all the pieces of received imaging technique information on the imaging technique selection screen 901.

Then, in step S602, examination information is created. The creation of examination information illustrated here includes the selection of a scheduled imaging technique. When an instruction for starting the examination is given, the operation unit 108 transmits an examination information confirmation notification including the examination information and the selected scheduled imaging technique to the input detection unit 4071. Upon receipt of the examination information confirmation notification, the input detection unit 4071 transmits the examination information confirmation notification to the examination control unit 406. Upon receipt of the examination information confirmation notification, the examination control unit 406 inputs the examination information and the scheduled imaging technique, which are included in the examination information confirmation notification, to the examination execution information generated at the time when the patient information is confirmed.

The flow of manually creating patient information, examination information, and a scheduled imaging technique is illustrated in steps S601 to S602, but is not limited thereto. Selecting work list information acquired from the HIS/RIS 114 enables patient information, examination information, and a scheduled imaging technique to be created at once. In this case, step S601 is omitted. When an instruction for starting the examination is given, the operation unit 108 transmits an examination information confirmation notification including patient information, examination information, and a scheduled imaging technique, which are included in the selected work list information, to the input detection unit 4071. The subsequent flow is similar to that described above.

Then, in step S603, an examination start process is carried out. When the creation of examination execution information is completed in step S602, the examination control unit 406 transmits an examination start notification to the examination information storage unit 403 and the display control unit 4070. The examination start notification includes examination-scheduled-to-be-conducted information. Upon receipt of the examination start notification, the examination information storage unit 403 registers the examination-scheduled-to-be-conducted information as new examination information. Then, the examination information storage unit 403 updates the examination status of the registered new examination information to "in progress". The examination status includes "not started", "in progress", "in suspension", and "end". Upon receipt of the examination start notification, the display control unit 4070 transmits an imaging screen transition notification to the display unit 109. The imaging screen transition notification includes the examination-scheduled-to-be-conducted information. Upon receipt of the imaging screen transition notification, the display unit 109 displays an imaging screen 1001. The display unit 109 displays, on the imaging screen 1001, the patient information, the examination information, and the imaging technique information included in the received examination information.

In step S604, an imaging technique with which imaging is executed next is selected from among the scheduled imaging techniques included in the started examination information. The selection of an imaging technique is selected by pressing an imaging technique display portion 1009 displayed on the imaging screen 1001. Upon acceptance of the pressing of an imaging technique button, the operation unit 108 transmits an imaging technique selection notification to the input detection unit 4071. The imaging technique selection notification includes selected imaging technique information. Upon receipt of the imaging technique selection notification, the input detection unit 4071 transmits an imaging technique selection notification to the examination control unit 406. The display control unit 4070 transmits an under-preparation-for-irradiation display notification to the display unit 109. Upon receipt of the under-preparation-for-irradiation display notification, the display unit 109 switches the display of a sensor status display portion 903 on the imaging screen 1001. Upon receipt of the imaging technique selection notification, the examination control unit 406 transmits an irradiation permission request notification to the imaging control unit 405. The irradiation permission request notification includes the selected imaging technique information. Upon receipt of the irradiation permission request notification, the imaging control unit 405 transmits the irradiation permission request notification to the communication circuit 112. Upon receipt of the irradiation permission request notification, the communication circuit 112 transmits the irradiation permission request notification to the X-ray control unit 104 and the X-ray detector 106. Upon receipt of the irradiation permission request notification, the X-ray control unit 104 notifies the X-ray generation unit 102 of the imaging conditions and position information included in the imaging technique information included in the irradiation permission request notification. Thereafter, when the setting of conditions for the X-ray generation unit 102 and the movement of the X-ray generation unit 102 to the initial position are completed, the X-ray control unit 104 transmits an irradiation permission notification to the communication circuit 112. The irradiation permission notification includes imaging technique information for which irradiation has been permitted. Upon receipt of the irradiation permission request notification, the X-ray detector 106 moves to the default position in accordance with the default position information included in the imaging technique information included in the irradiation permission request notification. When X-ray detection is ready for use, the X-ray detector 106 transmits an irradiation permission notification to the communication circuit 112. Upon receipt of the irradiation permission notifications from both the X-ray control unit 104 and the X-ray detector 106, the communication circuit 112 transmits an irradiation permission notification to the imaging control unit 405. Upon receipt of the irradiation permission notification, the imaging control unit 405 transmits the irradiation permission notification to the examination control unit 406. Upon receipt of the irradiation permission notification, the examination control unit 406 transmits the irradiation permission notification to the display control unit 4070. Upon receipt of the irradiation permission notification, the display control unit 4070 transmits an irradiation permission display notification to the display unit 109. Upon receipt of the irradiation permission display notification, the display unit 109 switches the display of the sensor status display portion 903 on the imaging screen 1001. Further, the display unit 109 displays an intended-for-imaging thumbnail 1012 in the imaging technique display portion 1009 on the imaging screen 1001. In the way described above, switching the display of the sensor status display portion 903 and the imaging technique display portion 1009 allows the viewer to easily identify that irradiation is available and distinguish the imaging technique for which an image is to be added in the next irradiation. While the flow of manual selection of an imaging technique has been described, the present invention also enables automatic selection of an imaging technique at the timing when the next imaging session is ready to start, such as at the start of an examination or at the end of irradiation. In this case, at the time when the next imaging session is ready to start, the examination control unit 406 acquires imaging technique information whose status is "imaging not yet started" from among the scheduled imaging technique information included in the examination-scheduled-to-be-conducted information. The status of the imaging technique information includes "imaging in progress" and "imaging completed" as well as "imaging not yet started". The examination control unit 406 selects the first registered imaging technique in the imaging technique information indicating "imaging not yet started", and transmits an irradiation permission request.

The method for selecting one imaging technique is not limited thereto. This can save the time taken for an operator to manually select the next imaging technique each time imaging is performed, and achieve smooth work flow.

In step S605, the object is placed. The placement of the object is performed by an operator or a person in charge of the examination. Step S605 may be performed before or after steps S601 to S604.

In step S606, a center position for reconstruction is set. Mainly the operator or the person in charge of the examination measures the center position (hereinafter, the isocenter position) on the basis of the region of interest of the object, and the isocenter position is input through the operation unit 108. When the input of the isocenter position is confirmed, the operation unit 108 transmits a center position confirmation notification to the input detection unit 4071. The center position confirmation notification includes isocenter position information. Upon receipt of the center position confirmation notification, the input detection unit 4071 transmits the center position confirmation notification to the examination control unit 406. Upon receipt of the center position confirmation notification, the examination control unit 406 transmits the center position confirmation notification to the imaging control unit 405. Upon receipt of the center position confirmation notification, the imaging control unit 405 inputs the isocenter position information to the position information included in the currently selected imaging technique information.

In step S607, positioning of the object with fluoroscopy is performed. In particular, since the influence of artifacts on tomosynthesis largely depends on the direction of X-rays with which the examinee is irradiated, fluoroscopy is used to check the placement of the patient to check whether the object has been placed in the correct position. When the X-ray irradiation switch 103 is pressed, the X-ray irradiation switch 103 transmits an irradiation start request to the X-ray control unit 104. Upon receipt of the irradiation start request, the X-ray control unit 104 transmits an irradiation start instruction to the X-ray generation unit 102. Upon acceptance of the irradiation start instruction, the X-ray generation unit 102 starts X-ray irradiation. Thereafter, the X-ray generation unit 102 transmits an irradiation start notification to the X-ray control unit 104. Upon receipt of the irradiation start notification, the X-ray control unit 104 transmits the irradiation start notification to the imaging control unit 405 via the communication circuit 112. Upon receipt of the irradiation start notification, the imaging control unit 405 transmits the irradiation start notification to which the currently selected imaging technique information is added to the examination control unit 406. Upon receipt of the irradiation start notification, the examination control unit 406 updates the status of the imaging technique for which irradiation has been started within the imaging technique information included in the examination-scheduled-to-be-conducted information to "imaging in progress". Further, the examination control unit 406 transmits the irradiation start notification to the display control unit 4070. Upon receipt of the irradiation start notification, the display control unit 4070 transmits an irradiation-in-progress display notification to the display unit 109. Upon receipt of the irradiation-in-progress display notification, the display unit 109 switches the display of the sensor status display portion 903 on the imaging screen 1001. Meanwhile, the X-ray detector 106 detects the emitted X-rays, and converts the X-rays into X-ray image data. Further, the X-ray detector 106 acquires position information in synchronization with the detection of the X-rays. The X-ray detector 106 transmits the X-ray image data and the position information to the imaging control unit 405 via the communication circuit 112. Upon receipt of the X-ray image data and the position information, the imaging control unit 405 inputs the position information to the currently selected imaging technique. Further, the imaging control unit 405 transmits the X-ray image data to the examination control unit 406. Upon receipt of the X-ray image data, the examination control unit 406 transmits the X-ray image data to the display control unit 4070. Upon receipt of the X-ray image data, the display control unit 4070 transmits the X-ray image data to the display unit 109. Upon receipt of the X-ray image data, the display unit 109 displays the X-ray image data in live view in an image display portion 1002 on the imaging screen 1001. Thereafter, when the X-ray irradiation switch 103 is released, the X-ray irradiation switch 103 transmits an irradiation stop request to the X-ray control unit 104. Upon receipt of the irradiation stop request, the X-ray control unit 104 transmits an irradiation stop instruction to the X-ray generation unit 102. Upon acceptance of the irradiation stop instruction, the X-ray generation unit 102 stops X-ray irradiation. Thereafter, the X-ray generation unit 102 transmits an irradiation end notification and an imaging execution condition notification to the X-ray control unit 104. The imaging execution condition notification includes imaging execution conditions and position information. Upon receipt of the irradiation end notification and the imaging execution condition notification, the X-ray control unit 104 transmits the irradiation end notification and the imaging execution condition notification to the imaging control unit 405 via the communication circuit 112. Upon receipt of the irradiation end notification and the imaging execution condition notification, the imaging control unit 405 transmits the irradiation end notification to which the currently selected imaging technique information is added and the imaging execution condition notification to the examination control unit 406. Upon receipt of the irradiation end notification, the examination control unit 406 updates the status of the imaging technique for which irradiation has been completed within the imaging technique information included in the examination-scheduled-to-be-conducted information to "imaging completed". Further, upon receipt of the irradiation implementation condition notification, the examination control unit 406 inputs the irradiation implementation conditions to the imaging technique for which irradiation has been completed within the imaging technique information included in the examination-scheduled-to-be-conducted information. At the same time, the examination control unit 406 transmits the irradiation end notification and the imaging execution condition notification to the display control unit 4070. Upon receipt of the irradiation end notification and the imaging execution condition notification, the display control unit 4070 transmits an irradiation end display notification and the imaging execution condition notification to the display unit 109. Upon receipt of the irradiation end display notification, the display unit 109 switches the display of the sensor status display portion 903 on the imaging screen 1001. Further, upon receipt of and the imaging execution condition notification, the display unit 109 updates the corresponding display annotation in an image display portion 902. While the case where the X-ray generation unit 102 simultaneously transmits an irradiation end notification and an imaging execution condition notification has been described, the present invention is not limited thereto. A notification of imaging execution conditions may be sent in real time during irradiation, or imaging execution conditions may be transmitted after the end of irradiation at a different timing from the transmission of an irradiation end notification. Alternatively, imaging execution conditions and position information may be transmitted at different timings.

Tomosynthesis imaging may not involve positioning with fluoroscopy. In this case, step S607 is omitted.

Figure 13:
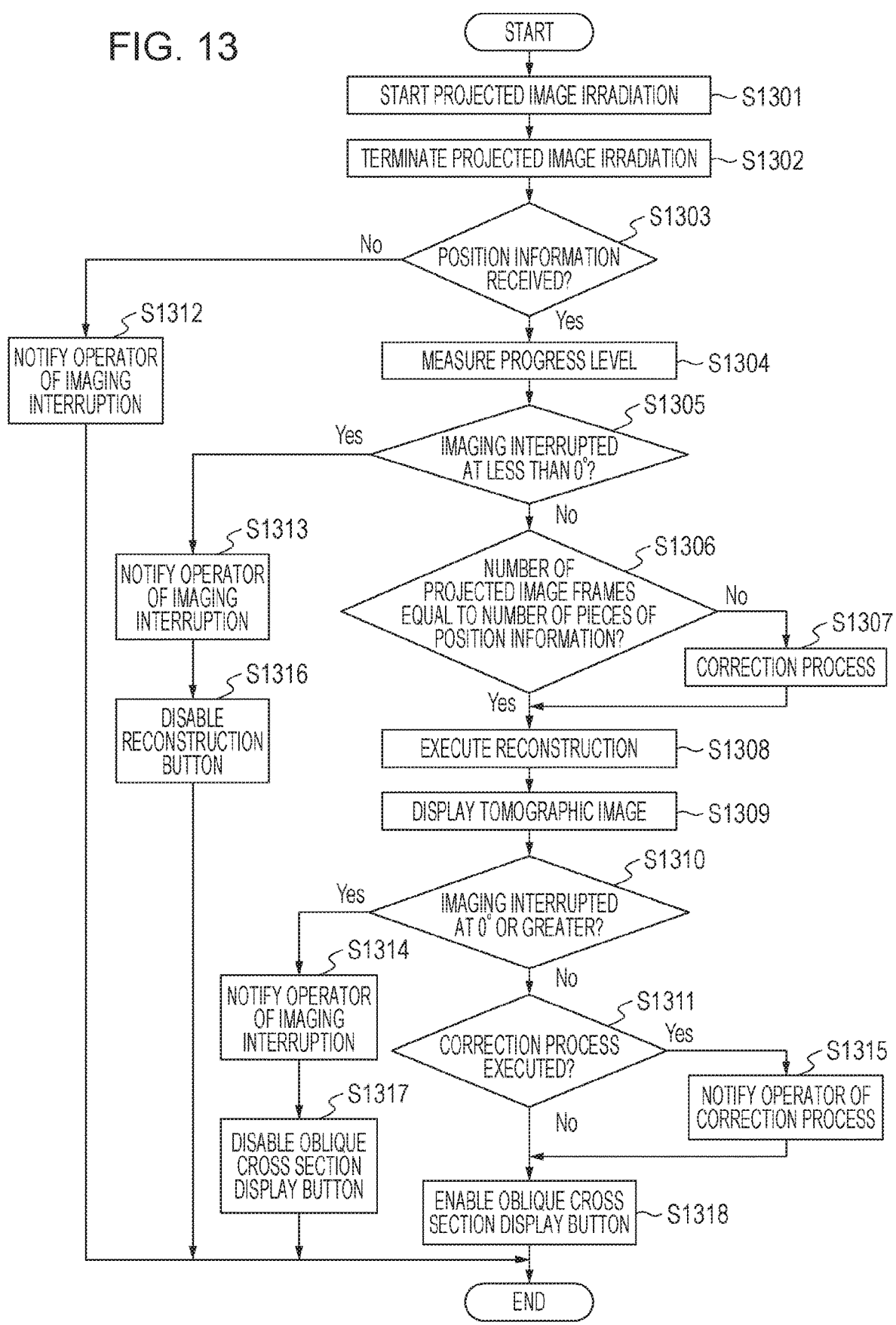
FIG. 13 is a flowchart diagram illustrating a process flow according to the embodiment of the present invention from the start of irradiation for projected images to the display of a reconstruction screen.

In step S608, projected images are captured. The process flow for the capture of projected images is almost similar to that with fluoroscopy in step S607. Note that, in the capture of projected images, upon receipt of the X-ray image data and the position information, the imaging control unit 405 inputs the position information to the currently selected imaging technique and saves the X-ray image data. In the present invention, furthermore, upon receipt of an irradiation end notification for projected images, the imaging control unit 405 determines the situation in which interruption of imaging is occurring from the position information. The imaging control unit 405 decides on whether a reconstruction process is available or not or whether the display of an oblique cross section is available or not in accordance with the situation in which interruption of imaging is occurring obtained as a result of the determination, and notifies the examination control unit 406 of the result (FIG. 13). This can prevent wasteful execution of reconstruction and prevent the display of an ineffective tomosynthesis image if the capture of projected images has been interrupted. This can also avoid the risk of false diagnosis by the reference to an oblique cross section with missing information.

In step S609, a reconstruction process is performed. Upon receipt of the X-ray image data of projected images and position information, the imaging control unit 405 transmits a reconstruction start notification to the display control unit 4070. At the same time, the imaging control unit 405 transmits a reconstruction request notification to the image processing unit 110. The reconstruction request notification includes the imaging technique information, the X-ray image data, and the position information. In this case, in the present invention, the imaging control unit 405 compares the number of frames of the X-ray image data of the projected images with the number of elements of position information. If both numbers are equal, the imaging control unit 405 transmits the reconstruction request notification as is. If there is a discrepancy between the numbers, the imaging control unit 405 performs a correction process to make the numbers match, and then transmits the reconstruction request notification (FIG. 13). This can also avoid the risk of failure of the reconstruction process if a discrepancy occurs between the number of frames of the X-ray image data and the number of elements of position information due to factors such as incorrect control of the X-ray generation unit 102 or the X-ray detector 106. Upon receipt of the reconstruction start notification, the display control unit 4070 transmits reconstruction screen display to the display unit 109. Upon receipt of the reconstruction screen notification, the display unit 109 displays a reconstruction screen 1101, and displays a progress bar on the image display portion 1002. Meanwhile, upon receipt of the reconstruction request notification, the image processing unit 110 performs a reconstruction process by using default reconstruction parameters in the imaging technique information, the position information, and the X-ray image data. When the reconstruction process is completed, the image processing unit 110 transmits a reconstruction completion notification to the imaging control unit 405. The reconstruction completion notification includes the generated tomosynthesis image, reconstruction parameters, and image processing parameters. Upon receipt of the reconstruction completion notification, the imaging control unit 405 transmits the reconstruction completion notification to the examination control unit 406.

Upon receipt of a reconstruction confirmation notification, the examination control unit 406 transmits a reconstruction end notification to the display control unit 4070. The reconstruction end notification includes imaging technique information in which the saved tomosynthesis image is present. Upon receipt of the reconstruction end notification, the display control unit 4070 transmits an imaging screen display notification to the display unit 109. Upon receipt of the imaging screen display notification, the display unit 109 shows a transition to the imaging screen 1001. At the same time, the display unit 109 adds a captured image thumbnail 1011 of the saved tomosynthesis image, and displays the captured image thumbnail 1011 as a preview.

In step S610, post-processing for tomosynthesis images is performed. The post-processing for tomosynthesis images includes the editing of cropped regions, parallel display (multi-view) of tomosynthesis images, a re-imaging process, and a reject process. When all the scheduled imaging techniques have been completed and the post-processing for tomosynthesis images has been completed, an examination end instruction is given. When an examination end instruction is given, the operation unit 108 transmits an examination end request notification to the input detection unit 4071. Upon receipt of the examination end request notification, the input detection unit 4071 transmits the examination end request notification to the examination control unit 406. Then, in step S611, an examination termination process is carried out. The examination control unit 406 transmits an examination end notification to the examination information storage unit 403 and the display control unit 4070. The examination end notification includes examination-scheduled-to-be-conducted information. At the same time, the examination control unit 406 transmits an image output notification to the image output control unit 409. The image output notification includes examination-scheduled-to-be-conducted information. Upon receipt of the examination end notification, the examination information storage unit 403 searches for and acquires examination-scheduled-to-be-conducted information from the registered examination information. Then, the examination information storage unit 403 updates the examination status in the acquired examination information to "end". Upon receipt of the examination end notification, the display control unit 4070 transmits the examination end notification to the display unit 109. Upon receipt of the examination end notification, the display unit 109 shows a transition to the patient information input screen 801. Also when the operation unit 108 accepts a suspension of the examination, a flow similar to that for the termination of the examination is used. Note that the examination information storage unit 403 updates the examination status in the acquired examination information to "in suspension". Then, in step S612, image output is carried out. Upon receipt of the image output notification, the image output control unit 409 performs an image output process for the output device 410 via the communication circuit 112.

Figure 6:
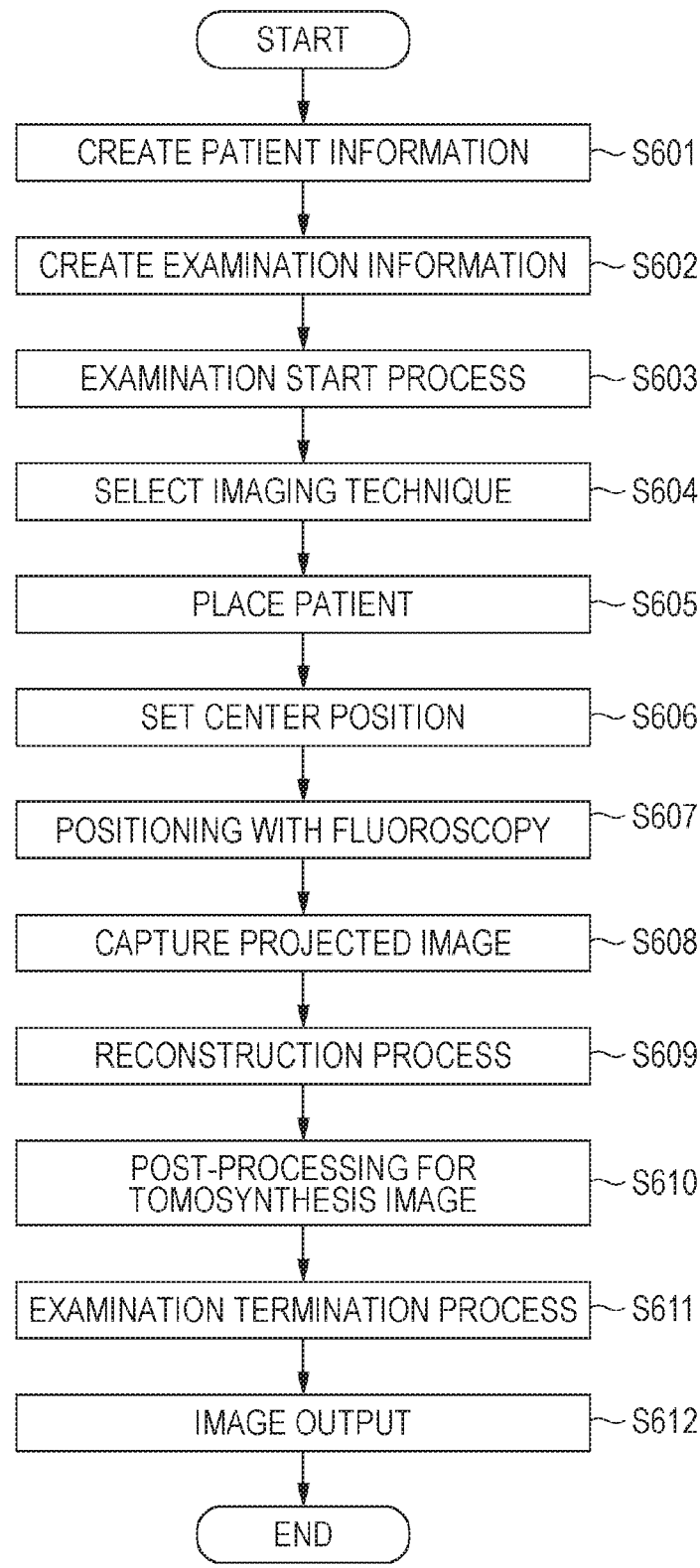
FIG. 6 is a flowchart diagram illustrating a process flow according to the embodiment of the present invention from the start to the end of an examination during tomosynthesis imaging.
Figure 7:
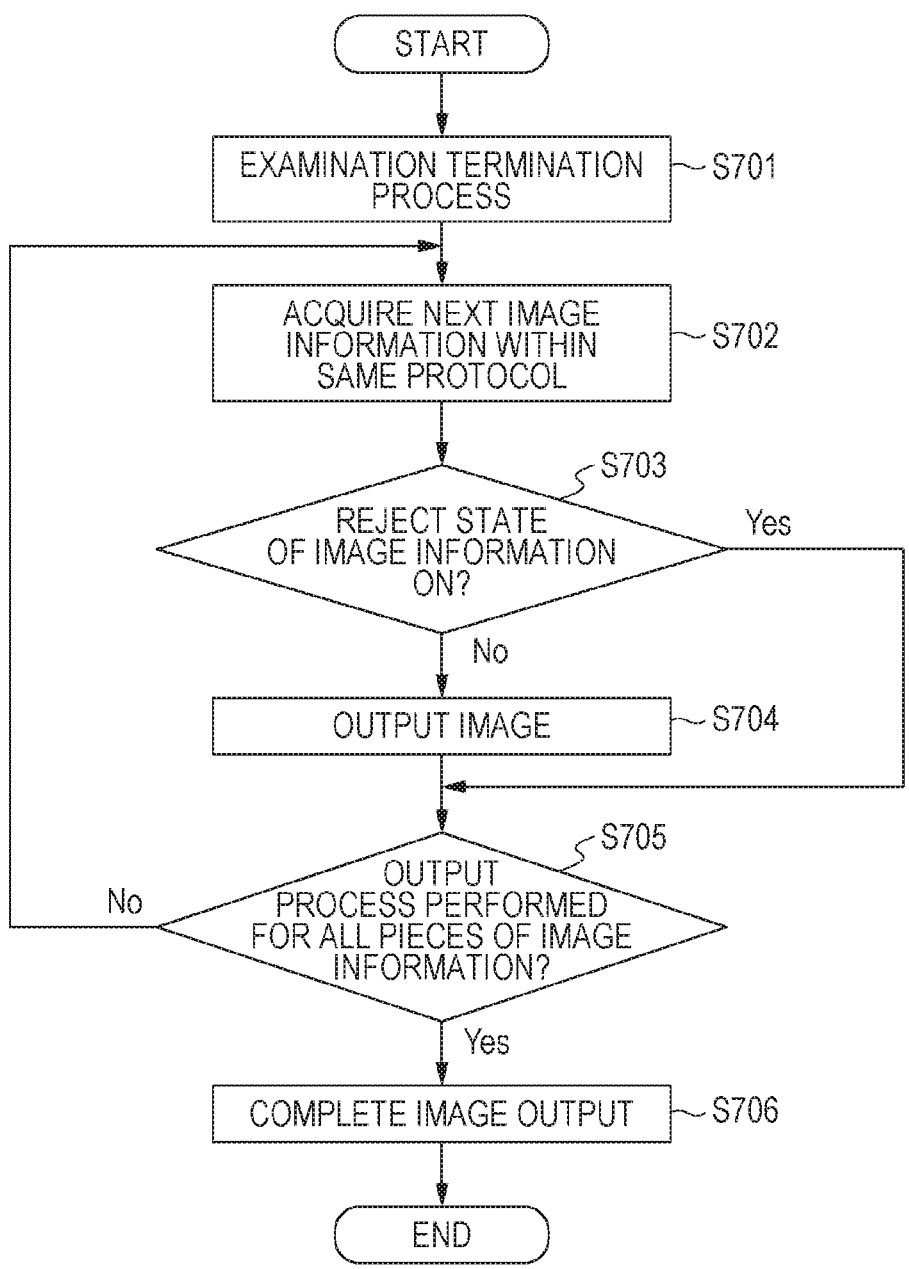
FIG. 7 is a flowchart diagram illustrating a process flow according to the embodiment of the present invention from the end of the examination to the completion of image output.

Here, the flow of an image output process in the present invention will be illustrated using FIG. 7. First, in step S701, an examination termination process is carried out. The examination termination process is similar to that in step S611 in FIG. 6. Then, in step S702, the image output control unit 409 acquires all the imaging techniques whose status is "imaging completed" from the examination-scheduled-to-be-conducted information included in the image output notification, and acquires the image information at the beginning. Then, in step S703, the image output control unit 409 checks the reject state of the acquired image information. If the reject state is OFF, the image output control unit 409 proceeds to step S704. In step S704, the image output control unit 409 transmits an image output request notification to the communication circuit 112. The image output request notification includes X-ray image data or tomosynthesis image data, and image information. At the same time, the image output control unit 409 sets the output state of the image information to ON. Upon receipt of the image output request notification, the communication circuit 112 outputs the image data or tomosynthesis image data included in the image output request notification to the output device 410. Then, in step S705, the image output control unit 409 checks whether or not an output process has been performed on all the pieces of image information acquired in step S702. If the output state of the image information is ON or the reject state is ON, the image output control unit 409 judges that an output process has been performed. If there is any image information on which no output process has been performed, the image output control unit 409 returns to step S702. If an output process has been performed on all the pieces of image information, the image output control unit 409 proceeds to step S706. Then, in step S706, the image output control unit 409 transmits an image output completion notification to the examination control unit 406. Thus, the image output process ends.

In the way described above, the image output control unit 409 limits the transmission of data set as a reject to an external device.

In the following, a description will be given of an example display screen displayed on the display unit 109 by the display control unit 4070.

Figure 8:
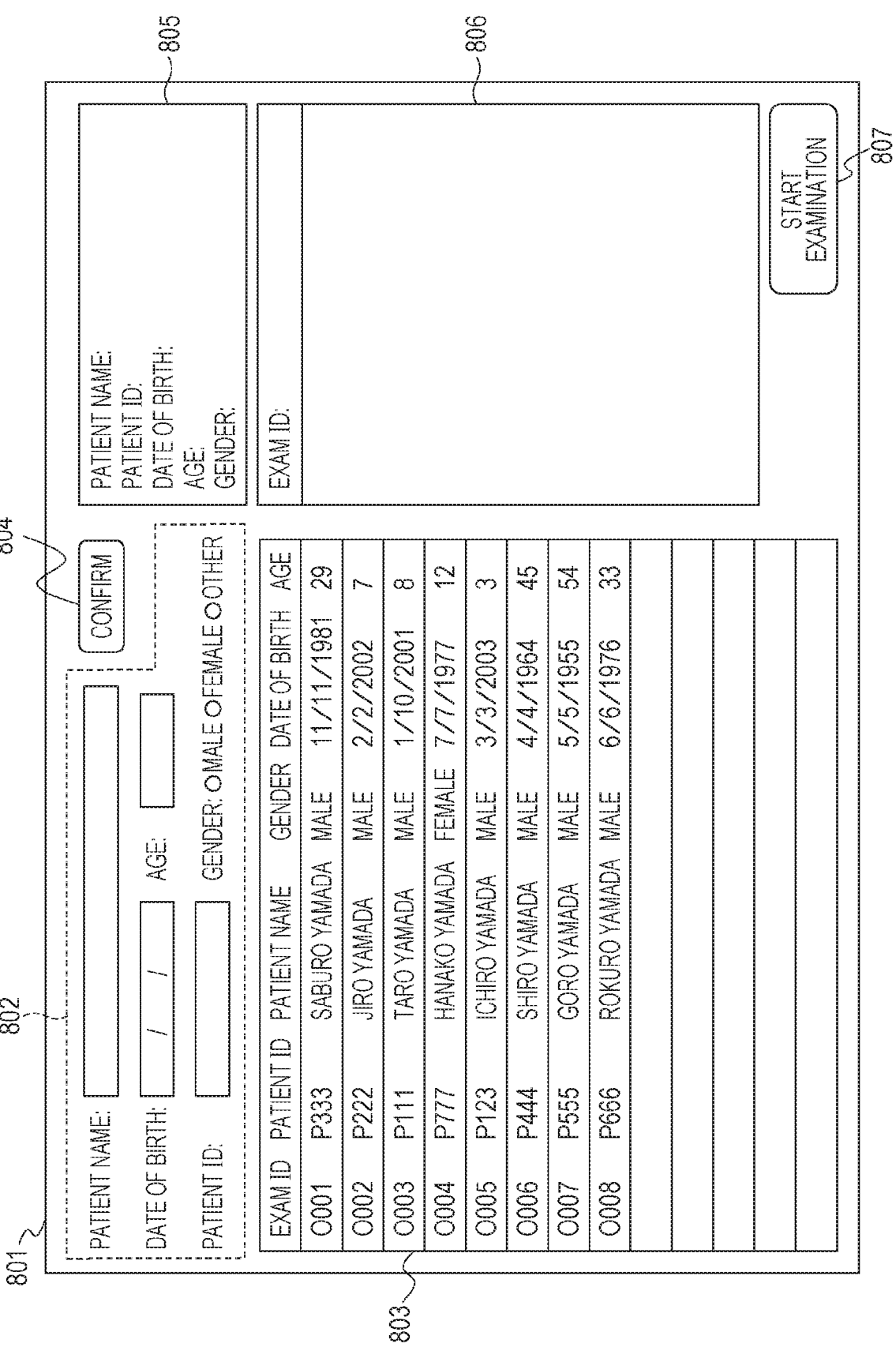
FIG. 8 is a diagram illustrating a patient information input screen according to the embodiment of the present invention.

An example of the patient information input screen 801 displayed in step S601 in FIG. 6 will be illustrated with reference to FIG. 8. The patient information input screen 801 is a screen on which information on a patient to be subjected to an examination is input. The patient information input screen 801 is constituted by a patient information input portion 802, a patient information list 803, a patient information confirmation instruction portion 804, a patient information display portion 805, an examination information display portion 806, and an examination start instruction portion 807. The patient information input portion 802 is an area in which values of items included in the patient information are input or selected. In the patient information list 803, pieces of patient information used for examinations conducted in the past are displayed in list form. The patient information list 803 has columns, each showing one of the items included in the patient information. The list has rows, each showing a piece of patient information on one patient. When an arbitrary one of the pieces of patient information in the list is selected, the selected piece of patient information is input to the respective entry portions in the patient information input portion 802. The patient information confirmation instruction portion 804 is a button for confirming the values input to the patient information input portion 802 as patient information. When the button is pressed, it is checked whether values have been input to required input items or whether the values input to the input items are correct or acceptable. If there is no problem, the values are confirmed as patient information. The patient information display portion 805 is an area in which confirmed patient information is displayed. No values are displayed in items until patient information is confirmed, and, at the time when patient information is confirmed, values are displayed. The examination information display portion 806 is an area in which input examination information is displayed. The examination information illustrated here includes information for identifying an examination, such as an examination ID, an inquiring physician's name, a radiologist's name, examination description, and a facility name. In addition, an imaging technique selected as intended for imaging is also included. Note that at least one or more imaging techniques are selectable per examination. The examination information display portion 806 has an area in which items in the examination information are displayed, and an area in which the selected imaging technique or imaging techniques are displayed. No values are displayed in the respective items until examination information is input. Likewise, no imaging techniques are displayed until any imaging technique is selected. Values and an imaging technique are respectively displayed when examination information is input and at the time when the imaging technique is selected. In addition, a plurality of examinations can be conducted at once in a single imaging session. In this case, a number of examination information display portions 806 corresponding to the number of examinations are displayed side by side. The examination start instruction portion 807 is a button for providing an instruction to start an examination. When the button is pressed, it is checked whether patient information and examination information have been input and, in addition, whether one or more imaging techniques have been selected for each examination. If there is no problem, an examination start process is carried out. If there is any examination for which no imaging technique has been selected, the imaging technique selection screen 901 is displayed.

Figure 9:
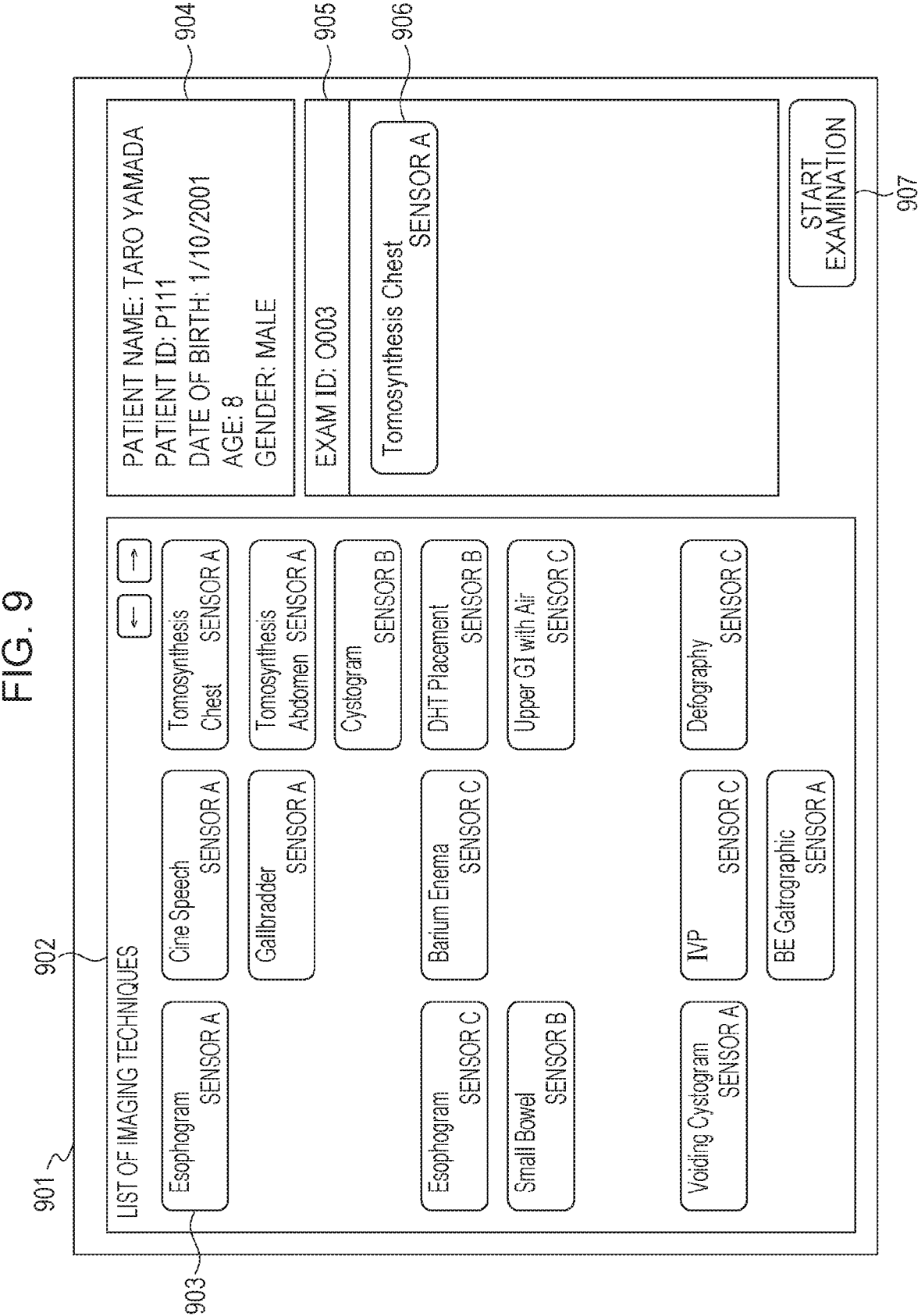
FIG. 9 is a diagram illustrating an imaging technique selection screen according to the embodiment of the present invention.

Next, an example of the imaging technique selection screen 901 displayed in step S602 in FIG. 6 is illustrated using FIG. 9. The imaging technique selection screen 901 is a screen on which an imaging technique intended for imaging in an examination to be conducted is selected. The imaging technique selection screen 901 is constituted by an imaging technique display portion 902, imaging technique buttons 903, a patient information display portion 904, an examination information display portion 905, a selected imaging technique button 906, and an examination start instruction portion 907. The imaging technique display portion 902 is an area in which the imaging techniques saved in the imaging technique information storage unit 402 are displayed one by one by using the imaging technique buttons 903. The locations where the buttons are displayed can be changed as desired. In addition, one page is not sufficient to display all the buttons, the buttons can be displayed over a plurality of pages, in which case the display pages are switched in response to an instruction to switch between pages. The imaging technique buttons 903 are buttons each displayed for one of the imaging techniques saved in the imaging technique information storage unit 402. Each imaging technique button shows the name of an imaging technique and the name of a sensor to be used. When any button is pressed, the selected item is confirmed as intended for imaging in the currently selected examination. The patient information display portion 904 is an area in which confirmed patient information is displayed. The examination information display portion 905 is an area in which input examination information is displayed. As the selected imaging technique button 906, an imaging technique button 903 selected in the imaging technique display portion 902 is displayed. Since one or more imaging techniques are selectable for each examination, another selected imaging technique button 906 is added to the bottom of the examination information display portion 905 each time an imaging technique button is selected. The examination start instruction portion 807 is a button for providing an instruction to start an examination. When the button is pressed, it is checked whether patient information and examination information have been input and, in addition, whether one or more imaging techniques have been selected for each examination. If there is no problem, an examination start process is carried out. When an examination start process is carried out, a transition to the imaging screen 1001 occurs. If there is any examination for which no imaging technique has been selected, the user is prompted to select any imaging technique, and no screen transition occurs. The imaging technique selection screen 901 having the configuration described above is displayed.

Figure 10:
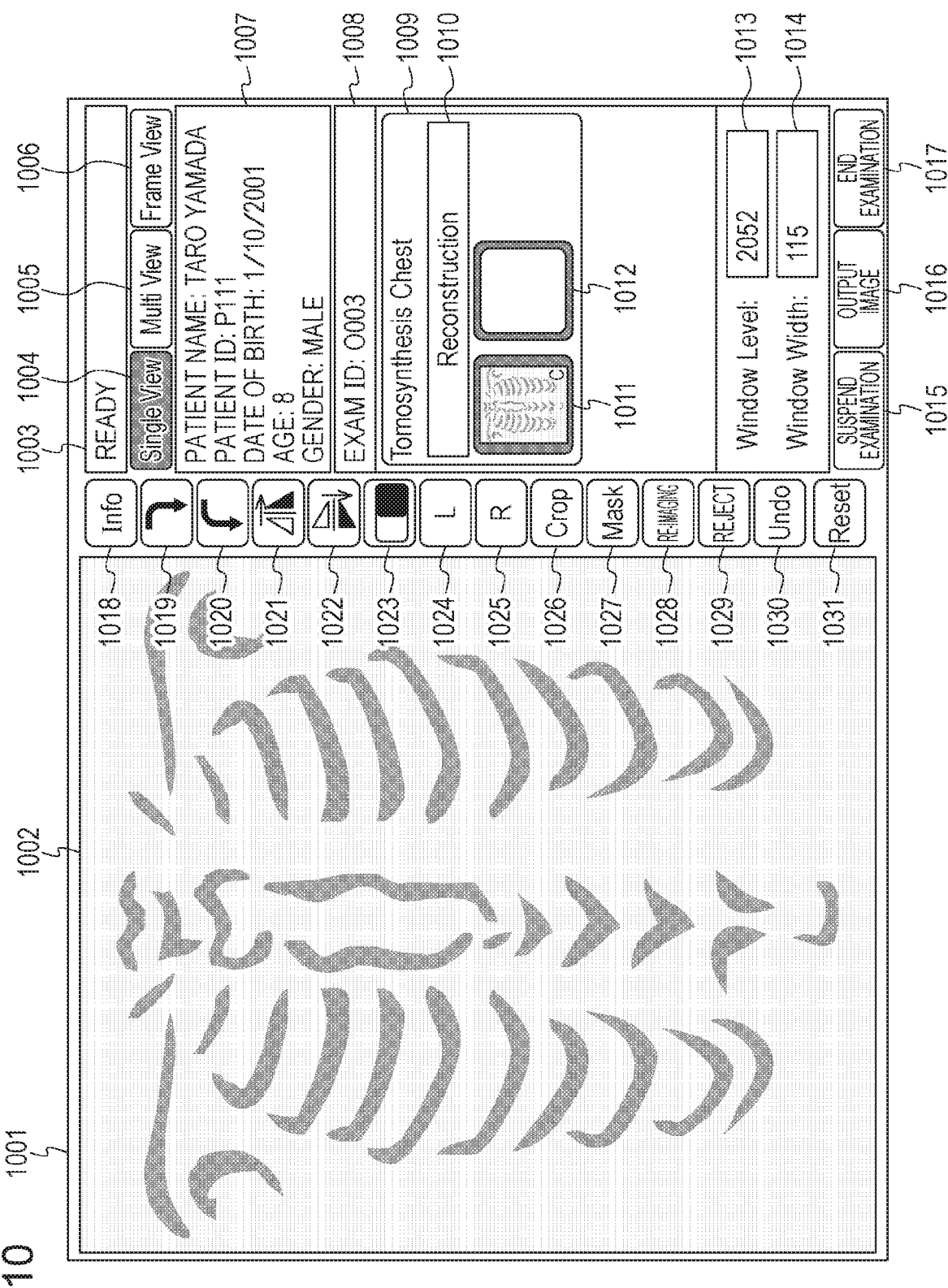
FIG. 10 is a diagram illustrating an imaging screen according to the embodiment of the present invention.

Next, an example of the imaging screen 1001 displayed in step S603 in FIG. 6 is illustrated using FIG. 10. The imaging screen 1001 is constituted by an image display portion 1002, a status display portion 1003, a single-view instruction portion 1004, a multi-view instruction portion 1005, a frame-view instruction portion 1006, a patient information display portion 1007, an examination information display portion 1008, an imaging technique display portion 1009, a reconstruction instruction portion 1010, a captured image thumbnail 1011, an intended-for-imaging thumbnail 1012, a window level editing portion 1013, a window width editing portion 1014, an examination suspension instruction portion 1015, an image output instruction portion 1016, an examination termination instruction portion 1017, an annotation display instruction portion 1018, a clockwise instruction portion 1019, a counterclockwise instruction portion 1020, a horizontal inversion instruction portion 1021, a vertical inversion instruction portion 1022, a white/black inversion instruction portion 1023, an L mark placement instruction portion 1024, an R mark placement instruction portion 1025, a cropping setting instruction portion 1026, a mask processing instruction portion 1027, a re-imaging button 1028, a reject button 1029, an undo instruction portion 1030, and a reset instruction portion 1031. The image display portion 1002 shows a preview of a captured image obtained after still-image imaging or a tomosynthesis image subjected to the reconstruction process. During moving-image imaging, captured images are displayed as previews in real time. If preview selection is switched after imaging, a captured image subjected to preview selection is displayed as a preview. In addition, patient information, examination information, irradiation conditions, and so forth are displayed as annotations in accordance with the settings. No images are displayed in the initial state immediately after the start of an examination. The status display portion 1003 is an area in which the status notified by the X-ray control unit 104 or the X-ray detector 106 is displayed using a distinct color or text to allow the operator to distinguishably identify the status. Upon receipt of a notification of a status from the X-ray control unit 104 or the X-ray detector 106 via the communication circuit 112, the imaging control unit 405 notifies the examination control unit 406 of a change of the status. The examination control unit 406 determines the displayed content in accordance with a combination of statuses of the X-ray control unit 104 or the X-ray detector 106, and transmits a status display switching instruction to the display control unit 4070. For example, if the X-ray control unit 104 is not capable of X-ray irradiation or the X-ray detector 106 is not capable of X-ray detection, "Not Ready" is displayed on the sensor status. If the X-ray control unit 104 is capable of X-ray irradiation and the X-ray detector 106 is capable of X-ray detection, "Ready" is displayed on the sensor status and the background color is changed to a color which is made easily distinguishable from that for the display of "Not Ready". The single-view instruction portion 1004 is a button for switching to a single-view mode in which one frame of an image being selected as a preview is displayed in the image display portion 1002. In the case of images of a plurality of frames, it is also possible to display a different frame or reproduce a moving image during the display of a preview in accordance with a keyboard or mouse operation. The multi-view instruction portion 1005 is a button for switching to a multi-view mode in which the image display portion 1002 is segmented into a plurality of display areas in a lattice pattern and images captured in the examination being conducted are displayed in parallel. The button is disabled and the multi-view mode is not available until two or more images are captured in the examination being conducted. The frame-view instruction portion 1006 is a button for switching to a frame-view mode in which the image display portion 1002 is segmented into a plurality of display areas in a lattice pattern and frame images of a moving image being selected as a preview are displayed in parallel. If the image being selected as a preview is not a moving image, the button is disabled and the frame-view mode is not available. The patient information display portion 1007 is an area in which patient information such as the patient's name and a patient ID is displayed. The examination information display portion 1008 shows examination information such as an examination ID or examination description. Further, imaging techniques selected in the examination are displayed side by side in the imaging technique display portion 1009. The imaging technique display portion 1009 includes the reconstruction instruction portion 1010, the captured image thumbnail 1011, and the intended-for-imaging thumbnail 1012. The imaging technique display portion 1009 shows imaging technique information such as the name of an imaging technique and all the captured image thumbnails 1011 that have been implemented. In the initial state immediately after the start of an examination, no imaging has been performed and thus no captured image thumbnails 1011 are displayed. The reconstruction instruction portion 1010 is a button for providing an instruction to execute a reconstruction process on a tomosynthesis imaging technique including the image currently being selected as a preview. The reconstruction instruction portion 1010 is not displayed for imaging techniques other than tomosynthesis, and the display area is cut out. If a plurality of tomosynthesis imaging techniques are being displayed, all the buttons other than a tomosynthesis imaging technique including the image currently being selected as a preview are disabled. An instruction is given through the reconstruction instruction portion 1010, thereby enabling reconstruction to be re-performed on a tomosynthesis imaging technique which has been subjected to a reconstruction process once. The captured image thumbnail 1011 has displayed thereon a thumbnail image corresponding to each captured image, an imaging type mark, a similarity mark 2301, and a reject mark 2701. The imaging type mark is a mark that makes the types of still-image imaging, fluoroscopic imaging, cine imaging, and tomosynthesis-image imaging distinguishable from one another. For example, cine imaging is represented by "C" and tomosynthesis-image imaging is represented by "T". However, the marks are not limited thereto, and any sign capable of distinguishing imaging types from one another may be used. Selecting the captured image thumbnail 1011 switches preview display. Further, the imaging technique display portion 1009 currently being selected as intended for the next irradiation shows the intended-for-imaging thumbnail 1012, which is displayed as blank, at a location where an additional thumbnail is to be placed when irradiation takes place next time. When the state of being selected as intended for irradiation is released, the intended-for-imaging thumbnail 1012 is made invisible. The window level editing portion 1013 and the window width editing portion 1014 are portions in which the window level and the window width of the image currently being selected as a preview are edited. Changing the values displayed in the edit boxes or dragging the mouse on the image display portion 1002 applies the editing to an image being displayed as a preview. The examination suspension instruction portion 1015 is a button for providing an instruction to suspend the examination being conducted. The examination control unit 406 performs an examination suspension process. The image output instruction portion 1016 is a button for providing an instruction to output a captured image included in the examination being conducted. A process flow when an image output instruction is given is similar to that for the image output process at the end of the examination illustrated in FIG. 7. The examination termination instruction portion 1017 is a button for providing an instruction to terminate the examination being conducted. The examination control unit 406 performs an examination termination process. The annotation display instruction portion 1018 is a button for switching the visibility of an annotation displayed in the image display portion 1002. The clockwise instruction portion 1019 is a button for allowing a captured image being displayed as a preview to rotate clockwise. The counterclockwise instruction portion 1020 is a button for allowing a captured image being displayed as a preview to rotate counterclockwise. The horizontal inversion instruction portion 1021 is a button for horizontally inverting a captured image being displayed as a preview. The vertical inversion instruction portion 1022 is a button for vertically inverting a captured image being displayed as a preview. The white/black inversion instruction portion 1023 is a button for inverting the window value of a captured image being displayed as a preview. The L mark placement instruction portion 1024 is a button for placing the laterality marker "L" on a captured image being displayed as a preview. The button is on/off switchable, where "L" is placed when the button is on and "L" is removed when the button is off. The R mark placement instruction portion 1025 is a button for placing the laterality marker "R" on a captured image being displayed as a preview. The button is on/off switchable, where "R" is placed when the button is on and "R" is removed when the button is off. The cropping setting instruction portion 1026 is a button for providing an instruction to set the cropping settings for a region of interest in a captured image being displayed as a preview. The mask processing instruction portion 1027 is a button for providing an instruction to perform mask processing on a captured image being displayed as a preview. The re-imaging button 1029 is a button for providing an instruction to perform re-imaging on an imaging technique including an image currently being selected as a preview. The term re-imaging, as used herein, refers to a process for executing a reject process on an image specified in a re-imaging instruction and newly adding the same imaging technique. The reject button 1029 is a button for providing a reject instruction for an image currently being selected as a preview. When a reject process is executed, a reject setting included in the image information is switched to ON. The undo instruction portion 1030 is a button for providing an instruction to perform undo processing to return a history of processes on an image currently being selected as a preview to a new order. The reset instruction portion 1031 is a button for providing an instruction to perform a reset process for discarding all the processes for an image currently being selected as a preview and returning the state to a state obtained immediately after imaging. The imaging screen 1001 having the configuration described above is displayed.

The display control unit 4070 causes an imaging technique for capturing a projected image group to be displayed in the imaging technique display portion 1009 (first display area) on the foregoing imaging screen 1001. In response to the capture of a projected image group corresponding to the imaging technique, a captured image thumbnail 1011 representing the projected image group is displayed in the imaging technique display portion 1009. Further, in response to the generation of a tomosynthesis image based on the projected image group, the display control unit 4070 causes a captured image thumbnail 1011 of the tomosynthesis image to be displayed in the imaging technique display portion 1009 (first display area). Doing so provides an intelligible display of imaging information and its corresponding projected image group and tomosynthesis image.

Figure 11:
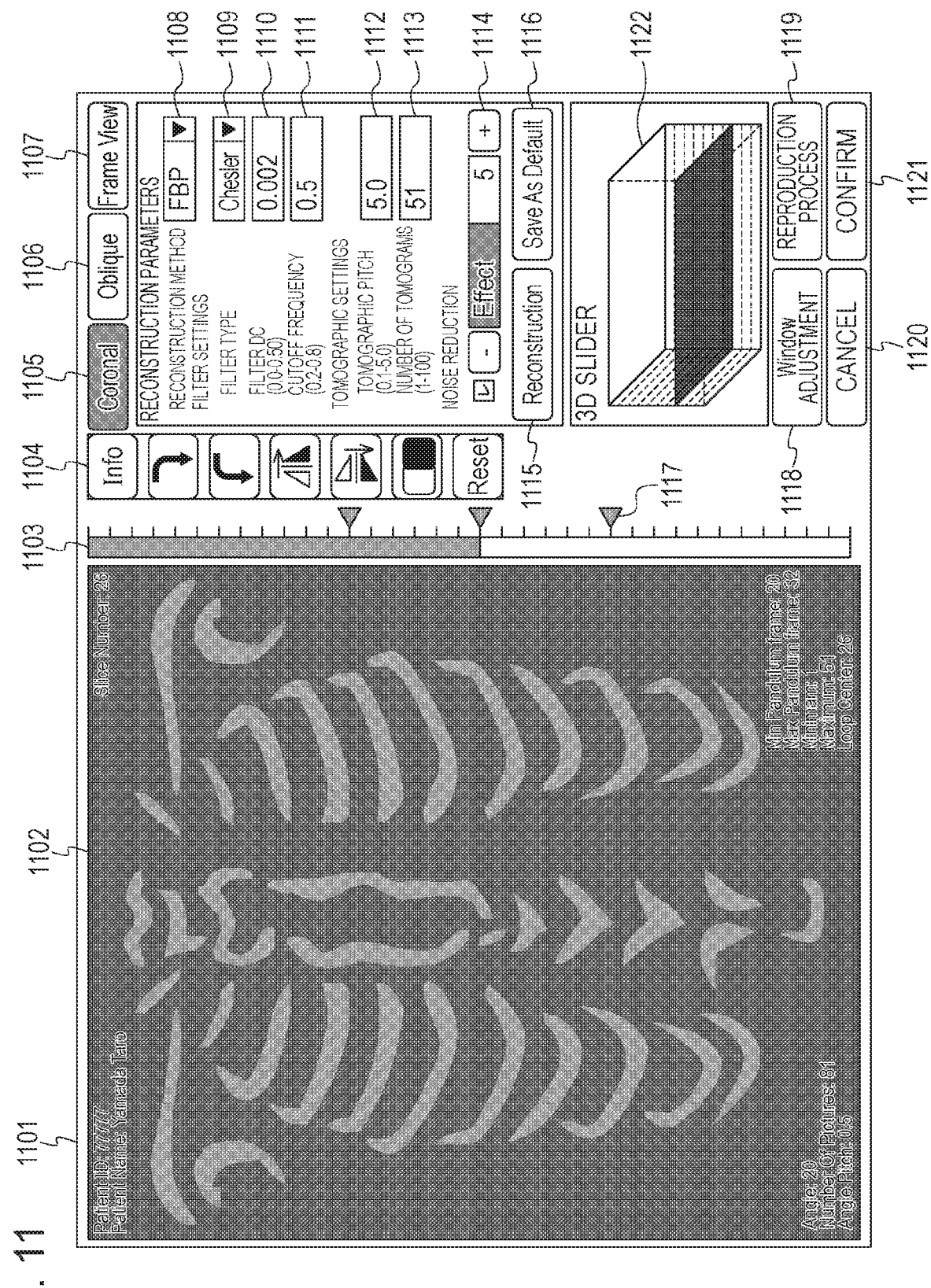
FIG. 11 is a diagram illustrating a reconstruction screen according to the embodiment of the present invention.

Next, an example of the reconstruction screen 1101 displayed in step S609 in FIG. 6 is illustrated using FIG. 11. The reconstruction screen 1101 is constituted by an image display portion 1102, a frame specifying slider 1103, an image operation toolbar 1104, a coronal cross section display instruction portion 1105, an oblique cross section display instruction portion 1106, a frame-view instruction portion 1107, a reconstruction method selection portion 1108, a reconstruction filter type selection portion 1109, a reconstruction filter DC editing portion 1110, a cutoff frequency editing portion 1111, a tomographic pitch editing portion 1112, a number-of-slice editing portion 1113, a noise reduction process editing portion 1114, a reconstruction process instruction portion 1115, a default settings instruction portion 1116, a frame reproduction range setting portion 1117, a window adjustment display instruction portion 1118, a reproduction process display instruction portion 1119, a reconstruction cancellation instruction portion 1120, a reconstruction confirmation instruction portion 1121, and a 3D slider 1122. The image display portion 1102 shows a preview of a tomosynthesis image subjected to the reconstruction process. During the ongoing reconstruction process, a progress bar notifying the user that the reconstruction process is in progress is displayed, and a tomosynthesis image is displayed at the same time as the completion of the reconstruction process. The frame specifying slider 1103 is used to check a frame image being displayed in a tomosynthesis image being displayed as a preview and to switch between frame images. At the same time as the display of a preview of the tomosynthesis image, memories for all the valid frames of the tomosynthesis image being displayed as a preview are equally displayed from the upper end to the lower end along the slider. Control is performed so that only valid frames can be specified, thereby reducing the risk of erroneous display of invalid frames. A frame having a number corresponding to a memory selected by selection or dragging across the frame specifying slider 1103 is displayed in the image display portion 1102. The image operation toolbar 1104 has arranged thereon controls for providing instructions to perform processes on the tomosynthesis image being displayed as a preview. The arranged controls are similar to 918 to 931 on the imaging screen 1001.

The coronal cross section display instruction portion 1105 is a button for providing an instruction that the tomosynthesis image displayed in the image display portion 1102 be displayed on a coronal cross section, and corresponds to a button for providing an instruction to display a first two-dimensional tomographic image. This button is made selectable in the initial state where the reconstruction screen 1101 in FIG. 11 is displayed, and is also in an on state (selected state). The oblique cross section display instruction portion 1106 is a button for providing an instruction that the tomosynthesis image displayed in the image display portion 1102 be displayed on an oblique cross section, and corresponds to a button for providing an instruction to display a second two-dimensional tomographic image.

The frame-view instruction portion 1107 is a button for switching to a frame-view mode in which the image display portion 1102 is segmented into a plurality of display areas in a lattice pattern and frame images of a tomosynthesis image being displayed as a preview are displayed in parallel. The button is disabled and frame-view display is not available during oblique cross section display. The reconstruction method selection portion 1108 is a control for selecting a reconstruction method such as the FBP (Filtered Back Projection) method, the shift-and-add method, or the iterative reconstruction method. The reconstruction filter type selection portion 1109 is a control for selecting the type of a filter to be used for the reconstruction process. The reconstruction filter DC editing portion 1110 is a control for editing the DC parameter for the filter to be used for the reconstruction process. The cutoff frequency editing portion 1111 is a control for editing the cutoff frequency of the filter to be used for the reconstruction process. The tomographic pitch editing portion 1112 is a control for editing the thickness between frames during the reconstruction process. The number-of-slice editing portion 1113 is a control for editing the total number of frames during the reconstruction process. The noise reduction process editing portion 1114 is a control for switching whether or not to apply a noise reduction process during the reconstruction process and for editing the degree of severity of the application of the noise reduction process. The reconstruction process instruction portion 1115 is a button for providing an instruction to execute a reconstruction process. Reconstruction is executed again by using a reconstruction parameter that has been input at the time when the button is pressed. In this case, the same projected images as those for the tomosynthesis image being displayed as a preview are used. The default settings instruction portion 1116 is a button for providing an instruction to change the default reconstruction parameters of the tomosynthesis imaging technique being displayed as a preview. When the button is pressed, a reconstruction parameter change notification together with the currently displayed reconstruction parameters is transmitted from the imaging control unit 405 to the examination control unit 406. The examination control unit 406 updates the reconstruction parameters of the tomosynthesis imaging technique which is the target of the reconstruction parameters, and transmits a "registration/update" process request to the imaging technique information storage unit 402. The frame reproduction range setting portion 1117 is a control for specifying a reproduction range during range-specified reciprocal reproduction. The frame reproduction range setting portion 1117 is constituted by knobs for specifying a minimum frame number, a center frame number, and a maximum frame number. Moving the respective knobs allows a range from the specified minimum frame number to the specified maximum frame number to be set as a reproduction range. The window adjustment display instruction portion 1118 is a button for switching the visibility of a window adjustment control. When the window adjustment display instruction portion 1118 is switched to ON, a window adjustment portion 1601 is displayed in the 3D slider 1122 display area.

The image processing unit 110 according to the embodiment performs an analysis process of a tomosynthesis image, and subjects a slice image generated from the tomosynthesis image, such as a coronal image or an oblique image, to tone conversion processing such as window processing. The display control unit 4070 causes the slice image subjected to the window processing to be displayed in the image display portion 1102 on the reconstruction screen 1101.

When the window adjustment display instruction portion 1118 is switched to OFF, the window adjustment portion 1601 is made invisible and the 3D slider 1122 is displayed. The reproduction process display instruction portion 1119 is a button for switching the visibility of a reproduction process control. When the reproduction process display instruction portion 1119 is switched to ON, a reproduction processing portion 2001 is displayed in the 3D slider 1122 display area. When the reproduction process display instruction portion 1119 is switched to OFF, the reproduction processing portion 1601 is made invisible and the 3D slider 1122 is displayed. The reconstruction cancellation instruction portion 1120 is a button for providing an instruction to discard the tomosynthesis image being previewed. When an instruction for canceling reconstruction is given, step S609 is completed without the storage of the tomosynthesis image and the image information, and a transition to the imaging screen 1001 occurs. On the imaging screen 1001, an image which has been previewed before the reconstruction screen is displayed is continuously selected as a preview. The reconstruction confirmation instruction portion 1121 is a button for providing an instruction to confirm the storage of the tomosynthesis image being previewed. When an instruction for confirming the storage is given, the tomosynthesis image being previewed is saved in the HDD 504. Thereafter, step S608 is completed, and a transition to the imaging screen 1001 occurs.

The 3D slider 1122 is a control for providing a pseudo-3D display of a frame of the generated tomosynthesis image and specifying a display frame. The 3D slider 1122 has displayed thereon ruled lines depicting a relative positional relationship between frames of each tomosynthesis image, and a small image is displayed at the position of the same frame number as a display frame image. Selecting a ruled line on the 3D slider 1122 or dragging the mouse can facilitate switching between display frames. As the ruled lines displayed on the 3D slider 1122, those for only valid frames of a tomosynthesis image are displayed. In addition, in association with the editing of the tomographic pitch or the number of slices, the positional relationship between frames of each tomosynthesis image subjected to the reconstruction process is displayed as a preview so as to be superimposed on the current state. This enables the operator to easily understand a change in thickness when changing the tomographic pitch or the number of slices. The reconstruction screen 1101 having the configuration described above is displayed.

Figure 12:
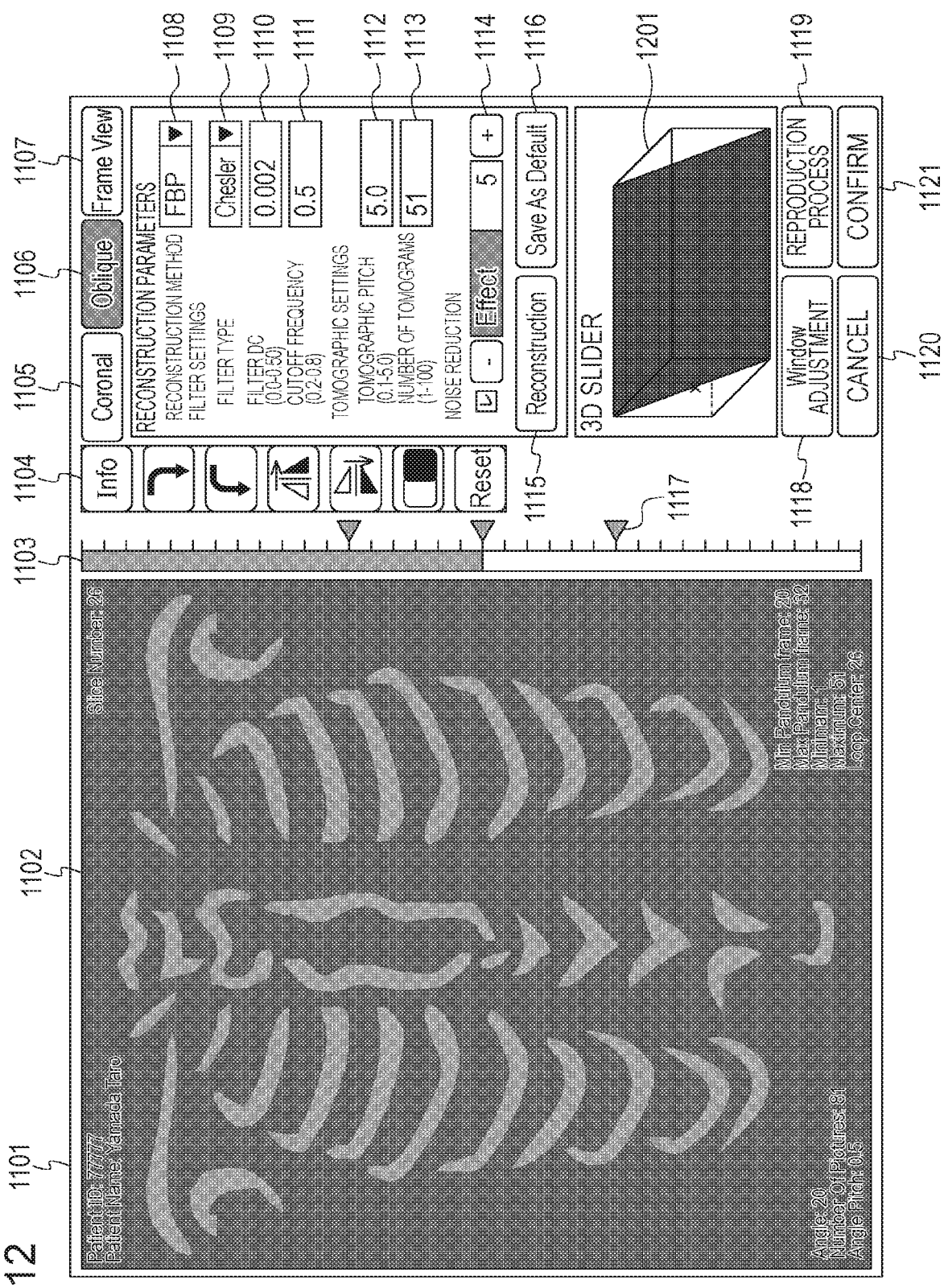
FIG. 12 is a diagram illustrating an oblique cross section display screen on the reconstruction screen according to the embodiment of the present invention.

Next, the reconstruction screen 1101 displayed in step S609 in FIG. 6 for the display of an oblique cross section is illustrated using FIG. 12. When the oblique cross section display instruction portion 1106 is pressed, the cross section of the tomosynthesis image displayed in the image display portion 1102 is switched from a coronal cross-sectional image to an oblique cross-sectional image. When the coronal cross section display instruction portion 1105 is pressed, the cross section of the tomosynthesis image displayed in the image display portion 1102 is switched from a coronal cross section to an oblique cross section. During the display of an oblique cross section, the specification of a frame by using the frame specifying slider 1103 or any reproduction instruction from the reproduction processing portion 1901 is ignored. In addition, the frame-view instruction portion 1107 is disabled, and the frame-view mode is not available. During the display of an oblique cross section, an oblique-angle editing 3D slider 1201 is displayed in place of the typical 3D slider 1122. The oblique-angle editing 3D slider 1201 is a display area in which posture information of an oblique cross-sectional image displayed in the image display portion 1102 appears. In the oblique-angle editing 3D slider 1201, a direction along an upper surface and a lower surface of an illustrated rectangular parallelepiped corresponds to the direction of a coronal cross-sectional image, and a presentation of posture information of an oblique cross-sectional image crossing the coronal cross-sectional image is provided.

Further, the oblique cross-sectional image illustrated in FIG. 12 is an image of a cross section that always extends through the isocenter. The isocenter is represented as a cross mark on a side surface of the illustrated rectangular parallelepiped. In another embodiment, the image processing unit 110 generates an oblique cross-sectional image at a position that does not pass through the isocenter, and the display control unit 4070 can cause the oblique cross-sectional image to be displayed in accordance with the operation input from the operation unit 108.

The editing of the display angle of a frame image displayed on the oblique-angle editing 3D slider 1201 results in the oblique angle being changed accordingly. In association with the oblique angle edited in the oblique-angle editing 3D slider 1201, the oblique angle of the tomosynthesis image displayed as a preview in the image display portion 1102 is also changed. The reconstruction screen 1101 having the configuration described above for the display of an oblique cross section is displayed.

<Oblique Display Limitation Process>

Here, an example of a process related to the display of a reconstruction screen from the start of irradiation for projected images, which is executed in step S608 and step S609 in FIG. 6, is illustrated using FIG. 13. The process illustrated in FIG. 13 is performed by, for example, the imaging control device 107 illustrated in FIG. 1. First, in step S1301, the irradiation switch 103 is pressed to start irradiation, and projected images are sequentially captured.

In S1302, the pressing of the irradiation switch 103 is released to terminate irradiation, and the capture of projected images is completed. Upon receipt of a projected image irradiation end notification, the imaging control unit 405 transmits an imaging interruption determination request notification to the imaging interruption determination unit 401. The imaging interruption determination request notification includes image information on the projected images, and position information.

Here, the imaging interruption determination unit 401 determines the situation in which interruption of imaging is occurring by using the image information on the projected images and the position information, and notifies the imaging control unit 405 of an imaging interruption determination result. The imaging interruption determination result includes a determination status, the determination status including "no position information", "interrupted in initial stage", "interrupted in later stage", and "completed".

In step S1303, upon receipt of the imaging interruption determination request notification, the imaging interruption determination unit 401 checks the position information. If no position information is included, the imaging interruption determination unit 401 sets the determination status to "no position information", and transmits the imaging interruption determination result to the imaging control unit 405.

If position information is included, in step S1304, the progress level measuring unit 4011 checks the imaging state. The progress level measuring unit 4011 refers to either the imaging angle included in the position information or the X-ray detector moving distance, and determines a maximum value (FIG. 3). If the maximum value is a negative value, the imaging interruption determination unit 401 determines interruption of the imaging at less than 0°, and sets the determination status to "interrupted in initial stage". If the initial position at the start of imaging begins with a positive value, the imaging interruption determination unit 401 refers to either the imaging angle included in the position information or the X-ray detector moving distance, and determines a minimum value. If the minimum value is a positive value, the imaging interruption determination unit 401 determines that the imaging has been interrupted at less than 0°, and sets the determination status to "interrupted in initial stage". Subsequently, the progress level measuring unit 4011 compares the maximum value of the imaging angle or X-ray detector moving distance with the maximum imaging angle included in the default imaging conditions or the maximum X-ray detector moving distance. If the maximum value of the position information is less than the maximum imaging angle or the maximum X-ray detector moving distance by a certain threshold value, the imaging interruption determination unit 401 determines interruption of the imaging at 0° or greater, and sets the determination status to "interrupted in later stage". If the minimum value of the imaging angle or X-ray detector moving distance is used, the minimum value is compared with the minimum imaging angle included in the default imaging conditions or the minimum X-ray detector moving distance. Thereafter, the imaging interruption determination unit 401 transmits the imaging interruption determination result to the imaging control unit 405.

Upon receipt of the imaging interruption determination result, the imaging control unit 405 checks the determination status. If the determination status indicates "no position information", "interrupted in initial stage", or "interrupted in later stage", the imaging control unit 405 transmits an imaging interruption notification to the examination control unit 406. Upon receipt of the imaging interruption notification, the examination control unit 406 updates the status of the target imaging technique information.

Then, in step S1305, the examination control unit 406 checks the status of the imaging technique information.

If the status indicates "no position information" in step S1305, then in step S1312, the examination control unit 406 displays a pop-up screen 1401 on the imaging screen 1001. When the pop-up screen 1401 is closed, the examination control unit 406 ends the process without a transition to a reconstruction screen.

If the status indicates "initial stage" in step S1305, then in step S1313, the examination control unit 406 displays a pop-up screen 1601 on the imaging screen 1001. When the pop-up screen 1601 is closed, the examination control unit 406 transmits a reconstruction prohibition notification to the display control unit 4070 without a transition to a reconstruction screen. The reconstruction transmission notification includes imaging technique information.

Then, in step S1316, upon receipt of the reconstruction prohibition notification, the display control unit 4070 transmits the reconstruction prohibition notification to the display unit 109. Upon receipt of the reconstruction prohibition notification, the display unit 109 disables the display of the reconstruction instruction portion 1010 in the imaging screen 1001, and then the process ends.

If the to-be-implemented determination status indicates "completed" in step S1305, then in step S1306, the imaging control unit 405 compares the number of acquired frames of projected images with the number of elements of position information.

If the number of acquired frames of projected images is different from the number of elements of position information in step S1306, then in step S1307, the imaging control unit 405 carries out a correction process to make the number of acquired frames of projected images and the number of elements of position information identical. At the same time, the imaging control unit 405 transmits a correction process accomplishment notification to the examination control unit 406. Upon receipt of the correction process accomplishment notification, the examination control unit 406 updates information on the presence or absence of a correction process for the target imaging technique information.

If the number of acquired frames of projected images and the number of elements of position information are identical in step S1306, no correction process is carried out.

In step S1308, the imaging control unit 405 carries out a reconstruction process. The process flow of steps S1308 to S1309 is similar to the process flow of S608 to S609 in FIG. 6. After a tomosynthesis image has been displayed on the reconstruction screen 1101, in step S1310, the examination control unit 406 checks the status of imaging technique information including the displayed tomosynthesis image.

In the way described above, even if the imaging ends in step S1302 due to the interruption of the imaging, in the situation where the imaging proceeds at 0° or greater (half or more finished), in S1308, the image processing unit 110 is caused to execute a reconstruction process on the basis of projected images obtained through the interrupted imaging. Then, a coronal image (first two-dimensional tomographic image) is displayed. In contrast, the display of an oblique image (second two-dimensional tomographic image) is prohibited, leading to less likelihood of false diagnosis.

In addition, in the way described above, even if the imaging ends in step S1302 due to the interruption of the imaging, the processes from step S1303 to step S1308 are sequentially executed, thereby enabling a reconstruction process to be started based on projected images obtained in accordance with the interrupted imaging. This enables a diagnostic image to be efficiently obtained while saving the time and labor of the operator.

Here, in another embodiment, only when the imaging ends due to the interruption of the imaging, the display control unit 4070 causes the display unit 109 to display a GUI for accepting an operation input indicating whether or not to start a reconstruction process before the image processing unit 110 executes the reconstruction process in step S1308. The GUI includes, for example, a message indicating "The imaging has been interrupted but you can perform a reconstruction process on a coronal image. Do you wish to start a reconstruction process?", and a pop-up window having an OK button and a Cancel button which can be pressed in accordance with an operation of the operation unit 108. This pop-up window is displayed superimposed on, for example, the examination screen illustrated in FIG. 10. When the input detection unit 4071 detects the pressing of the OK button in accordance with the operation input from the operation unit 108, the imaging control unit 405 causes the image processing unit 110 to start a reconstruction process in accordance with the detection. Doing so can reduce the execution of a reconstruction process unnecessary for the user, and achieve efficient execution of tomosynthesis imaging.

In step S1310, the display control unit 4070 limits the display of a two-dimensional tomographic image intersecting the detection surface of the X-ray detection unit in accordance with the degree of progress of imaging of projected images. If the status indicates "interrupted in later stage", in step S1314, the examination control unit 406 displays a pop-up screen 1601 on the reconstruction screen 1101. When the pop-up screen 1601 is closed, the examination control unit 406 transmits an oblique display prohibition notification to the display control unit 4070.

Then, in step S1317, upon receipt of the oblique display prohibition notification, the display control unit 4070 transmits the oblique display prohibition notification to the display unit 109. Upon receipt of the oblique display prohibition notification, the display unit 109 disables the display of the oblique display instruction portion 1106 on the reconstruction screen 1101, and limits the display of a two-dimensional tomographic image (second two-dimensional tomographic image, oblique image) intersecting the detection surface of the X-ray detector 106.

In the manner described above, if it is determined that the imaging has been interrupted by using the position information from the X-ray control unit 104, the display control unit 4070 performs control so that the oblique display instruction portion 1106 for providing an instruction to display an oblique image (second two-dimensional tomographic image) is not selectable. Accordingly, the display of an oblique image is prohibited. Doing so can reduce the probability that an image which is diagnostically inappropriate for the user will be displayed.

If the status does not indicate "interrupted in later stage" in step S1310, then in step S1311, the examination control unit 406 checks information on the presence or absence of a correction process for the imaging technique information.

If a correction process is present in step S1311, then in step S1315, the examination control unit 406 displays a pop-up screen 1701 on the reconstruction screen 1101. When the pop-up screen 1701 is closed, the examination control unit 406 transmits an oblique display permission notification to the display control unit 4070.

In step S1318, upon receipt of the oblique display permission notification, the display control unit 4070 transmits the oblique display permission notification to the display unit 109. Upon receipt of the oblique display permission notification, the display unit 109 enables the display of the oblique display instruction portion 1106 on the reconstruction screen 1101, and then the process ends.

In the example described above, after the image processing unit 110 has carried out a reconstruction process of three-dimensional volume data in S1308, the display control unit 4070 limits display in S1317 or the like. However, the embodiment is not limited thereto. In another exemplary embodiment, prior to the process of step S1318, the image processing unit 110 directly reconstructs a plurality of oblique images (second two-dimensional tomographic images) from projected images. This allows oblique images to be directly reconstructed from projected images, and can improve image quality. On the other hand, if the process proceeds to step S1314, the oblique image generation process is not performed by the control of the imaging control unit 405. By doing so, no generation process is performed for unnecessary oblique images, leading to efficient processing.

An example of the pop-up screen 1401 displayed on the reconstruction screen 1101 when it is judged in step S1312 in FIG. 13 that there is no notification of position information is illustrated using FIG. 14(a). The pop-up screen 1401 is displayed on the imaging screen 1001. The pop-up screen 1401 shows a message indicating that reconstruction is not available since there is no notification of position information, and an OK button 1402. When the OK button 1402 is pressed, the pop-up screen 1401 is closed, making an operation available on the imaging screen 1001. The pop-up screen 1401 having the configuration described above is displayed. Note that position information may possibly be transmitted later with a delay. Accordingly, the display of the reconstruction process instruction portion 1010 is enabled, and, if a notification of position information has been received at the time of pressing, reconstruction is carried out. If no notification of position information has been received at the time of pressing, the pop-up screen 1401 is displayed again.

Figure 14:
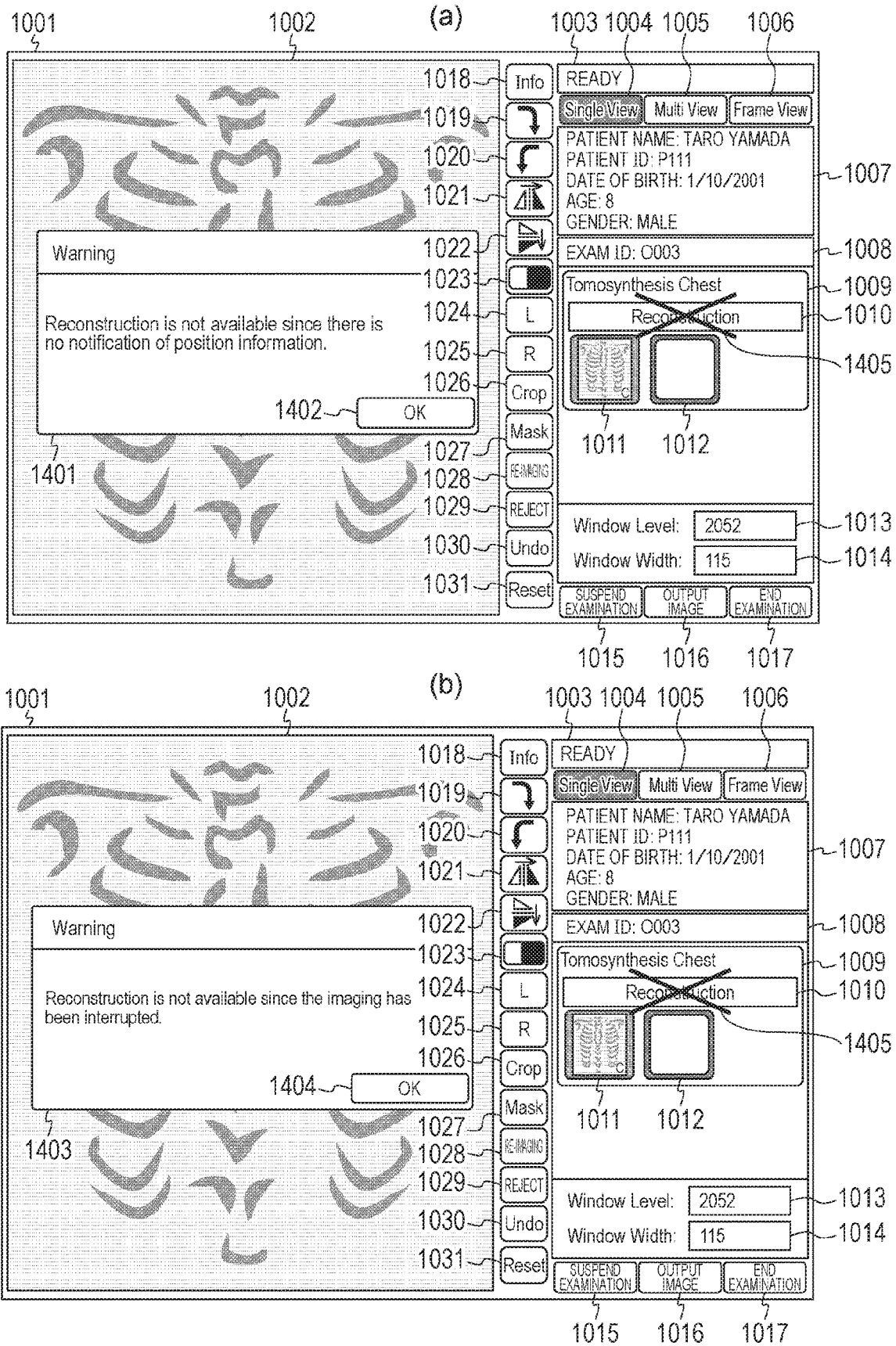
FIG. 14(a) is a diagram illustrating the imaging screen according to the embodiment of the present invention in a case where there is no notification of position information.
FIG. 14(b) is a diagram illustrating the imaging screen according to the embodiment of the present invention in a case where imaging is interrupted at less than 0°.

An example of a pop-up screen 1403 displayed on the reconstruction screen 1101 when it is judged in step S1313 in FIG. 13 that the capture of projected images has been interrupted at less than 0° is illustrated using FIG. 14(*b*). The pop-up screen 1403 is displayed on the imaging screen 1001. The pop-up screen 1403 shows a message indicating that reconstruction is not available since the imaging has been interrupted, and an OK button 1404. When the OK button 1404 is pressed, the pop-up screen 1401 is closed, making an operation available on the imaging screen 1001. In addition, for an imaging technique for which the capture of projected images has been interrupted at less than 0°, the reconstruction process instruction portion 1010 is disabled, and it is not possible to execute reconstruction. For example, displaying a cross mark 1405 over the reconstruction process instruction portion 1010 enables the disablement of the reconstruction process instruction portion 1010 to be more clearly presented.

Figure 15:
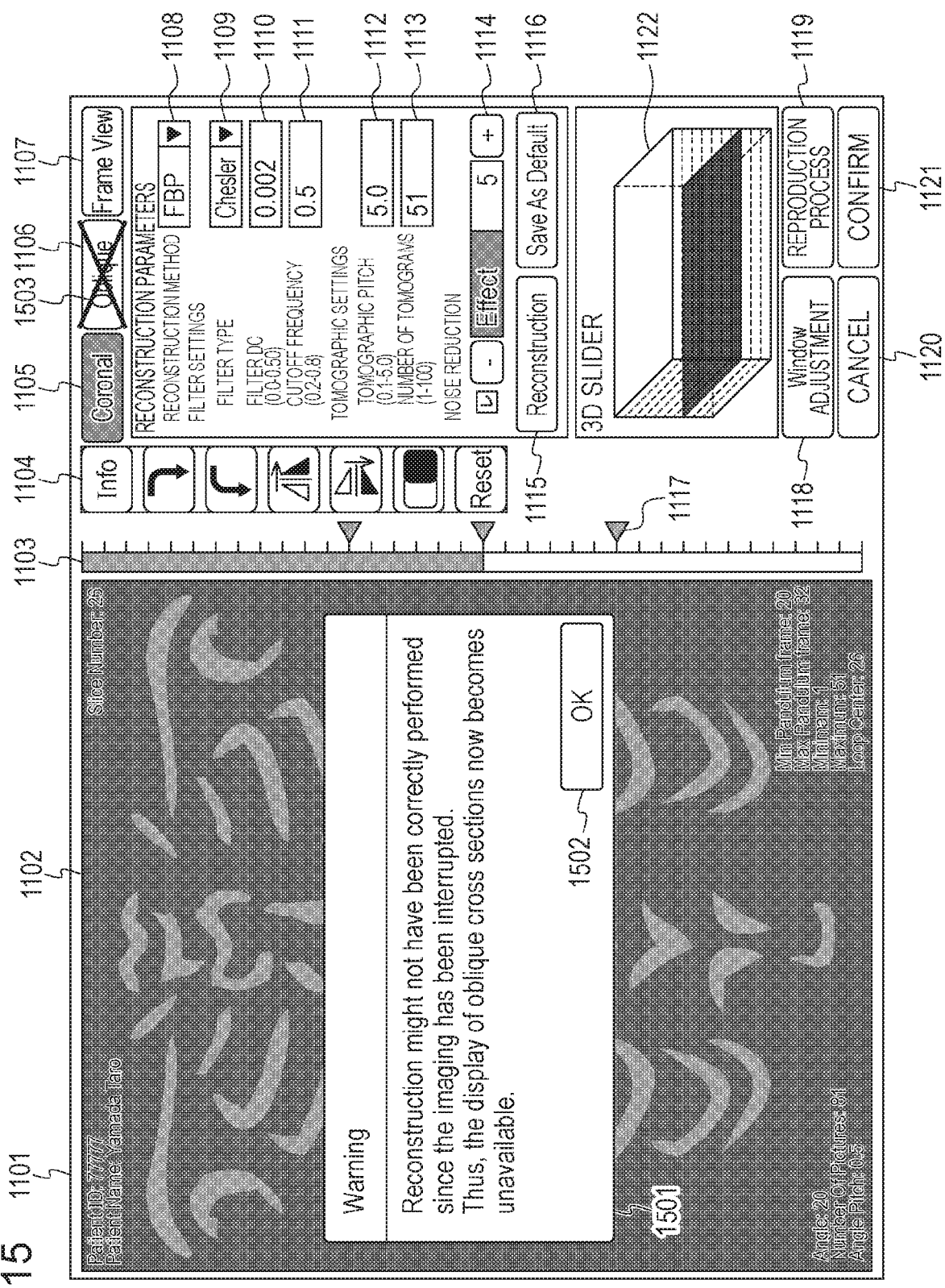
FIG. 15 is a diagram illustrating the reconstruction screen according to the embodiment of the present invention in a case where imaging is interrupted at 0° or greater.

Here, an example of a pop-up screen 1501 displayed on the reconstruction screen 1101 when the capture of projected images has been interrupted at 0° or greater in step S1314 in FIG. 13 is illustrated using FIG. 15. The pop-up screen 1501 is displayed on the reconstruction screen 1101. The pop-up screen 1501 shows a message indicating that reconstruction might not have been correctly performed since the imaging has been interrupted and that the display of oblique cross sections now becomes unavailable, and an OK button 1502. When the OK button 1502 is pressed, the pop-up screen 1501 is closed. In addition, if the capture of projected images has been interrupted at 0° or greater, the oblique cross section display instruction portion 1106 is disabled, making the display of an oblique cross section unavailable. For example, displaying a cross mark 1503 over the oblique cross section display instruction portion 1106 enables the disablement of the oblique cross section display instruction portion 1106 to be more clearly identified.

As in FIG. 14(*b*) and FIG. 15 described above, the display control unit 4070 causes a warning to be displayed at the time of the interruption of imaging, allowing it to be clarified that the imaging has been interrupted before the imaging of a predetermined range has been completed. In addition, as in FIG. 15, the display control unit 4070 causes a different warning to be displayed in accordance with the level of progress of imaging or the degree of advancement, allowing the user to readily recognize that a different process has been performed in accordance with the degree of advancement.

In another embodiment, even if it is determined in step S1310 that an interruption has occurred in the situation of imaging at 0° or greater, the oblique cross section display button is not disabled. This implies that whether an image can be used for diagnosis or not is deferred to the judgment of a person who is responsible for diagnosis, and the display control unit 4070 causes the display unit 109 to display an oblique image based on an X-ray projected image obtained by exposing the person being examined to X-rays. In this case, the display control unit 4070 performs display control to, when displaying an oblique image, also display an indication of a diagnostically unsuitable image. For example, the indication of a diagnostically unsuitable image is, for example, a message indicating "The quality of reconstructed images might be affected as a result of the interruption of the desired imaging operation", and, in addition, the display control unit 4070 causes an oblique image to be displayed. Alternatively, in a case where an oblique image of a certain posture is output to outside as a DICOM image, the image processing unit 110 embeds the text message described above into the image as image data. This can lead to less likelihood of false diagnosis because such an image may be misinterpreted as an image captured through a correct procedure.

In another embodiment, for example, the following situation is considered. Settings are made such that projected images obtained at irradiation positions from −30° to +30° are captured. It is assumed that, because of the interruption of imaging, only projected images from −30° to +10° have been successfully obtained. In this case, it is considered that quality equal to or more than that for reconstructed images based on projected images obtained at irradiation positions from at least −10° to +10° is assured. In addition, in a case where projected images are obtained by imaging over a range of ±30°, it is assumed that the intersection angle of an oblique image can be varied up to ±30°. In a case where projected images are obtained by imaging over a range of ±10°, it is assumed that the intersection angle of an oblique image can be varied up to ±10°. In this case, the display control unit 4070 performs control so that an oblique image based on projected images obtained through the interrupted imaging described above has an intersection angle which is variable over a range of ±10°.

Accordingly, in the manner described above, if imaging is interrupted midway under a first imaging condition, this situation is handled similarly to that for a second imaging condition which at least provides equal or higher image quality based on projected images obtained before interruption and based on position information. Specifically, the display control unit 4070 causes the display of oblique images over a range similar to that when imaging is performed under the second imaging condition.

By doing so, even if imaging is interrupted, obtained X-ray projected images can be effectively utilized as long as image quality is assured.

In the embodiment described above, the communication circuit 112 of the imaging control device 107 transmits driving conditions and also transmits irradiation conditions for the X-ray generation unit 102. However, the embodiment is not limited thereto. For example, irradiation conditions for the X-ray generation unit may be directly input through an operation unit (not illustrated) of the X-ray control unit 10, and the communication circuit 112 may receive the input irradiation conditions serving as setting conditions and irradiation conditions serving as execution information used for the actual imaging.

Examples of the reconstruction algorithm for the image processing unit 110 may also include the iterative reconstruction method in addition to the FBP method (Filtered Back Projection) and the shift-and-add method.

While the emission of pulsed X-rays has been described in the embodiment described above, this is not to be taken in a limiting sense. Alternatively, X-rays may be continuously emitted, and the X-ray detector may detect the X-rays to obtain projected images. In this case, the positions of the X-ray generation unit 102 and the X-ray detector 106 differ between at the start of X-ray irradiation and at the end of X-ray irradiation in terms of units of projected images. In this case, it may be sufficient to perform a reconstruction process by using a positional relationship obtained at a certain timing from the start of X-ray irradiation to the end of X-ray irradiation as geometric information for which the projected images have been captured.

In the embodiment described above, the processes in FIG. 6, FIG. 7, and FIG. 13 are executed by the imaging control device 107 illustrated in FIG. 1. However, the embodiment is not limited thereto. For example, an image processing device or an image management device, such as the PACS 115 or the viewer 116 illustrated in FIG. 1, may be configured to execute the processes according to the embodiment described above. The processes are executed by the imaging control device, enabling the X-ray imaging system 101 to make detailed studies and providing efficient imaging. Accordingly, repetitions of imaging can be reduced and efficient X-ray imaging can be achieved.

In the example described above, an embodiment of an X-ray imaging system has been illustrated, but is not limited thereto. Devices capable of tomosynthesis imaging or tomographic imaging, such as MRI, PET, and SPECT, or an image management device or an image processing device that handles images from such devices may implement the present invention.

As an alternative, any combination of the embodiments described above is also included in embodiments of the present invention. Alternatively, the case where the processes described above are executed in cooperation of a program with hardware is also included in an embodiment of the present invention. An embodiment of a program is implemented by a program for the processes described above, and by storing the program in a storage unit, loading the program onto a RAM by using a CPU of a system control unit, and executing instructions included in the program by using the CPU.

Figure 16:
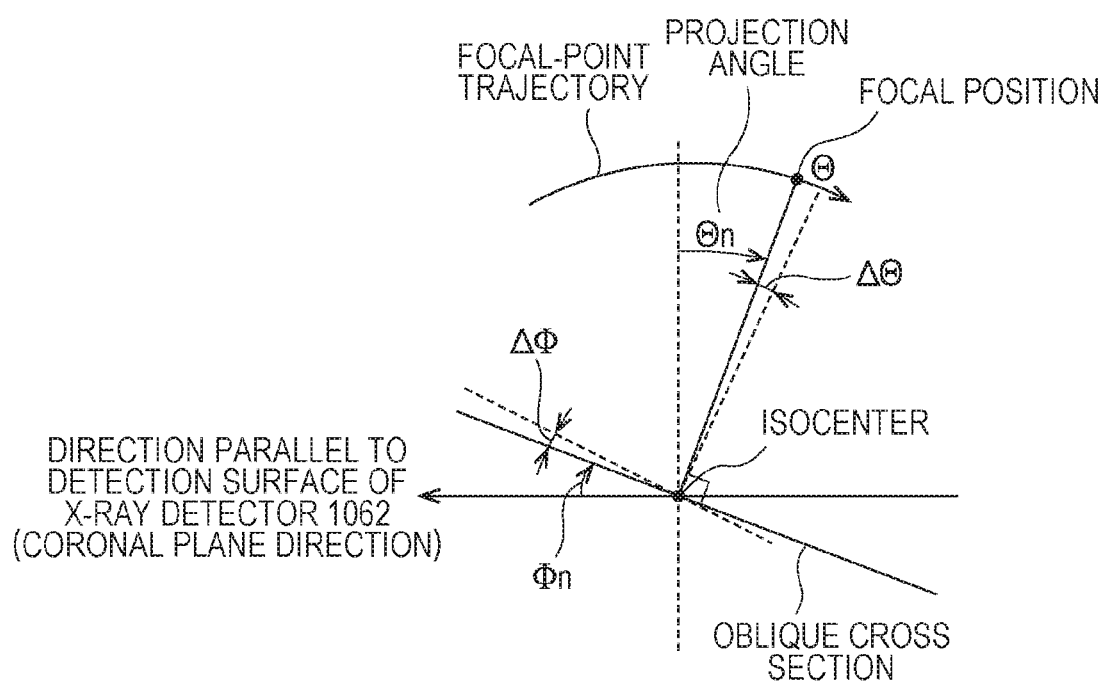
FIG. 16 is a diagram illustrating an example relationship between projection angles of projected images and oblique cross sections according to an embodiment.

Another embodiment will be described with reference to FIG. 16. The control unit 111 controls an angle interval $\Delta\Phi$ of oblique cross-sectional images O which are adjacent for the display of oblique cross-sectional images on the basis of an interval $\Delta\Theta$ of projection angles at which projected images P are captured (in the imaging system in FIG. 2, angles from −XX deg. to +XX deg.). Consideration is given to the case where, while the projection angle is changed over a range from the projection angle −XX deg. to the projection angle +XX deg., X-ray irradiation is performed N times to obtain N projected images P. The difference between the projection angle $\Theta n$ for the n-th (n<N−1) X-ray irradiation and the projection angle $\Theta n+1$ for the (n+1)-th X-ray irradiation is defined as $\Delta\Theta$. $\Delta\Theta$ may be constant regardless of n, or may be different for each n. Even if $\Delta\Theta$ is controlled to be constant regardless of n, resulting projected images may not exactly match due to any error caused by a motor and the like. For example, variations with errors less than or equal to 5% of $\Delta\Theta$ may be handled as identical.

The value of $\Delta\Theta$ may be calculated based on $\Theta n$. The value of $\Theta n$ is acquired from the X-ray control unit 104 or the movement mechanism control unit 1063 as geometric information for each projected image. Alternatively, the value of $\Delta\Theta$ may be directly acquired from the X-ray control unit 104 or the movement mechanism control unit 1063.

In one embodiment, if $\Delta\Theta$ is constant, the angle interval of oblique cross-sectional images is given by $\Delta\Phi=\Delta\Theta$, and serves as an angle interval over which oblique cross sections are sequentially displayed. For example, the mouse cursor is placed over the 3D slider in FIG. 12 or the 3D slider is selected to be in focus. In this case, it is assumed that an oblique cross-sectional image On oriented at an angle of $\Phi n$ with respect to the coronal plane (the detection surface of the X-ray detector) is being displayed. In this state, the up-arrow key on the keyboard is pressed once, thereby displaying an oblique cross-sectional image On+1 with an angle $\Phi n+1$ with respect to the coronal plane, which is given by $\Phi n+1−\Phi n=\Delta\Phi=\Delta\Theta$. In this case, desirably, $\Phi n=\Theta n$. By doing so, the oblique image O is an image of a cross section in an irradiation direction $\Theta$ which is the normal direction, resulting in an increase in the quality of the oblique image. Even if $\Phi n=\Theta n$ is not satisfied, reducing $\Delta$ of $\Phi n=\Theta n\pm\Delta$ to 25 percent or less of $\Delta\Theta$ can reduce the difference between $\Phi n$ and $\Theta n$, achieving the advantage of improving image quality compared to the case of exceeding 25%. Even if $\Delta\Theta$ is not constant, making $\Delta\Theta n$ and $\Delta\Phi n$ identical or reducing the difference between $\Phi n$ and $\Theta n$ can improve image quality.

In another embodiment, the control unit 111 causes the display of an oblique image of a cross section not passing through the isocenter. While an image of a cross section not passing through the isocenter provides improved quality for a tomosynthesis image, in some cases, a cross-sectional image passing through the isocenter may not necessarily be an image suitable for observation since the operator may wish to observe a fracture at a specific position in a specific direction, for example. For example, if a setting for displaying an oblique image of a cross section not passing through the isocenter is made, the display control unit 111 causes such an oblique image to be displayed, whereas if a setting for displaying an oblique image of a cross section not passing through the isocenter is not made, the display control unit 111 does not cause such an oblique image to be displayed. The setting information is stored in the memory of the imaging control device 107, and can be changed by a user in accordance with an operation through the operation unit 108. For an oblique image of a cross section not passing through the isocenter, which is displayed when a setting for displaying an oblique image of a cross section not passing through the isocenter is made, as described in the embodiment described above, the angle $\Phi$ with respect to the coronal plane is set to be equal to any of the projection angles $\theta$ of the projected images P, whereby the image quality can be guaranteed to some extent.

As an alternative, in step S608 described above, the display control unit 4070 causes the display unit 109 to sequentially display projected images upon sequentially receiving the projected images during the capture of projected images. This enables the user to make sure that successively captured projected images have no problem during imaging. In accordance with the completion of the capture of projected images in step S608, the image processing unit 110 executes a reconstruction process. In accordance with the completion of the reconstruction, the display control unit 4070 displays a tomosynthesis image obtained through the reconstruction on the display unit 109. The series of processes described above is controlled by the imaging control unit 405. Accordingly, a reconstruction process is performed in accordance with the completion of the capture of projected images, enabling a quick check of tomosynthesis images.

In the manner described above, the display of projected images during the capture of projected images helps the user easily check a problem regarding the capture of projected images. Quick display of a tomosynthesis image after the completion of the capture of projected images helps the user easily make sure that there is no problem in reconstruction. This facilitates checking whether or not re-imaging is necessary on the basis of both projected images and a reconstructed image.

In the embodiment described above, for example, the functions of the imaging control device 107 may be distributed to a plurality of devices capable of communicating with each other, thereby implementing the functions of the imaging control device 107 as a control system. For example, the functions of the image processing unit 110 may be provided for an external server, by way of example. The external server may be located in a control room or an imaging room where an X-ray imaging system for performing tomosynthesis imaging is installed, and may be connected via a dedicated LAN. The external server may also be located in the hospital, and may perform communication over a LAN in the hospital. Alternatively, the external server may be located in a data center or the like outside the hospital either locally or overseas, and data may be exchanged via secure communication methods such as VPN.

The present invention is not limited to the embodiments described above, and a variety of changes and modifications can be made without departing from the spirit and scope of the present invention. Therefore, to apprise the public of the scope of the present invention, the following claims are provided.

This application claims the benefit of Japanese Patent Application No. 2013-127978 filed Jun. 18, 2013, which is hereby incorporated by reference herein in its entirety.

The invention claimed is:

1. A control device for controlling tomosynthesis imaging for obtaining a tomographic image from a plurality of projected images captured by irradiating an object with X-rays from a plurality of irradiation angles by using an X-ray generation unit and an X-ray detection unit, the control device comprising:
   a memory storing a program; and
   one or more processors which, by executing the program, function as each unit comprising:
      an image processing unit configured to generate, on the basis of image data of the captured plurality of projected images, an oblique image which is a two-dimensional tomographic image along a plane intersecting a detection surface of the X-ray detection unit;
      an acquisition unit configured to acquire information on a range of irradiation angles of the X-ray generation unit relative to the X-ray detection unit used when each of the plurality of projected images is captured; and
      a display control unit configured to control a display unit to display the oblique image in accordance with the information on the range of irradiation angles of the X-ray generation unit and information about an oblique angle for generating the oblique image,
      wherein the display control unit limits the display of the oblique image so that the oblique angle does not exceed the range of irradiation angles.

2. The control device according to claim 1, further comprising a communication circuit that transmits a driving condition to the X-ray detection unit and that receives the plurality of projected images from the X-ray detection unit.

3. The control device according to claim 1, wherein the display control unit limits a range of intersection angles between the detection surface and the two-dimensional tomographic image to be displayed on the display unit.

4. The control device according to claim 1, wherein the display control unit prohibits display of the two-dimensional tomographic image.

5. The control device according to claim 1, further comprising a determination unit configured to determine whether, after imaging of the plurality of projected images has been started, the imaging has been interrupted before the imaging of a predetermined range is completed, wherein
   the display control unit limits the display of the two-dimensional tomographic image in a case where it is determined that the imaging has been interrupted.

6. The control device according to claim 1, wherein the display control unit causes the oblique image to be displayed in a first display area on a display screen of the display unit as a two-dimensional tomographic image along a plane intersecting the detection surface, and causes posture information of the oblique image to be displayed in a second display area on the display screen of the display unit.

7. The control device according to claim 1, wherein the display control unit causes a warning to be displayed in a case where the imaging has been interrupted.

8. The control device according to claim 1, wherein
   in a case where imaging of the plurality of projected images has been completed without interruption, the image processing unit starts a reconstruction process to generate the oblique image based on the image data of the plurality of projected images in accordance with the completion, and
   in a case where imaging of the plurality of projected images has been interrupted, the display control unit causes a GUI for accepting an operation input for providing an instruction as to whether or not to start a reconstruction process based on the plurality of projected images to be displayed on the display unit in accordance with the interruption.

9. An X-ray imaging apparatus comprising:
   the control device according to claim 1; and
   the X-ray detection unit.

10. An X-ray imaging system comprising:
    the control device according to claim 1;
    the X-ray detection unit;
    the X-ray generation unit; and
    the display unit.

11. The control device according to claim 2, wherein
    the communication circuit transmits an irradiation condition of an X-ray to the X-ray generation unit, and receives information on an irradiation direction in which the X-ray is emitted from the X-ray generation unit.

12. The control device according to claim 5, wherein
    the display control unit prohibits the display of the two-dimensional tomographic image in a case where it is determined that the imaging has been interrupted.

13. The control device according to claim 5, further comprising a measurement unit configured to measure a level of progress of imaging, wherein
    the display control unit prohibits the display of the two-dimensional tomographic image in a case where the level of progress is between a first threshold value and a second threshold value larger than the first threshold value.

14. The control device according to claim 5, wherein
    the image processing unit generates a first two-dimensional tomographic image along the detection surface of the X-ray detection unit and generates the oblique image as a second two-dimensional tomographic image along a plane intersecting the detection surface on the basis the image data of the captured plurality of projected images.

15. The control device according to claim 5, wherein in a case where it is determined that the imaging has been interrupted, the image processing unit executes a reconstruction process to generate the oblique image on the basis of image data of a projected image obtained through the imaging until the imaging has been interrupted.

16. The control device according to claim 5, wherein in response to interruption of the imaging, the image processing unit starts a reconstruction process to generate the oblique image based on image data of a projected image obtained through the imaging until the interruption.

17. The control device according to claim 14, wherein in a case where it is determined that the imaging has been interrupted, the display control unit causes the first two-dimensional tomographic image to be displayed, and limits display of the second two-dimensional tomographic image so that an intersection angle with respect to the detection surface does not exceed a predetermined threshold value.

18. The control device according to claim 14, further comprising a measurement unit configured to measure a level of progress of imaging, wherein
the display control unit is configured to perform control to cause the first two-dimensional tomographic image to be displayed on the display unit, and
the display control unit further prohibits display of the first two-dimensional tomographic image in a case where the level of progress is smaller than a first threshold value.

19. The control device according to claim 14, further comprising a setting unit configured to set a range of irradiation positions of X-rays emitted by the X-ray generation unit, wherein
in a case where the imaging has been interrupted after the imaging of the plurality of projected images up to a middle of the range of irradiation positions has completed, the display control unit causes a coronal image as the first two-dimensional tomographic image to be displayed, and prohibits display of the oblique image as the second two-dimensional tomographic image.

20. The control device according to claim 14, wherein
the display control unit causes buttons each for providing an instruction to display one of the first and second two-dimensional tomographic images to be displayed on the display unit, and
the display control unit further performs control to make the button for providing an instruction for the second two-dimensional tomographic image unselectable in accordance with the irradiation directions each corresponding to one of the plurality of projected images.

21. A control method for controlling tomosynthesis imaging for obtaining a tomographic image from a plurality of projected images obtained by irradiating an object with X-rays from a plurality of irradiation angles by using an X-ray generation unit and an X-ray detection unit, the control method comprising:
a step of acquiring the plurality of projected images, and information on a range of irradiation angles of the X-ray generation unit with respect to the X-ray detection unit with which the plurality of projected images are respectively captured;
a step of generating, on the basis of image data of the captured plurality of projected images, an oblique image which is a two-dimensional tomographic image along a plane intersecting a detection surface of the X-ray detection unit;
a step of acquiring information on the range of irradiation angles of the X-ray generation unit relative to the X-ray detection unit when each of the plurality of projected images is captured; and
a step of controlling a display of the oblique image in accordance with the information on the range of irradiation angles of the X-ray generation unit and information about an oblique angle for generating the oblique image,
wherein the step of controlling limits the display of the oblique image so that the oblique angle does not exceed the range of irradiation angles.

22. A non-transitory computer-readable medium storing thereon a program for causing a computer to execute the control method according to claim 21.

23. A control device for controlling tomosynthesis imaging for obtaining a tomographic image from a plurality of projected images captured by irradiating an object with X-rays from a plurality of irradiation angles by using an X-ray generation unit and an X-ray detection unit, the control device comprising:
a memory storing a program; and
one or more processors which, by executing the program, function as each unit comprising:
an image processing unit configured to generate, on the basis of image data of the captured plurality of projected images, an oblique image which is a two-dimensional tomographic image along a plane intersecting a detection surface of the X-ray detection unit;
an acquisition unit configured to acquire information on a range of irradiation angles of the X-ray generation unit relative to the X-ray detection unit used when each of the plurality of projected images is captured; and
a display control unit configured to control whether or not the image processing unit executes a process for generating the oblique image in accordance with the information on the range of irradiation angles of the X-ray generation unit and information about an oblique angle for generating the oblique image,
wherein the oblique angle does not exceed the range of irradiation angles.

24. A control method for controlling tomosynthesis imaging for obtaining a tomographic image from a plurality of projected images obtained by irradiating an object with X-rays from a plurality of irradiation angles by using an X-ray generation unit and an X-ray detection unit, the control method comprising:
a step of acquiring the plurality of projected images, and information on a range of irradiation angles of the X-ray generation unit with respect to the X-ray detection unit with which the plurality of projected images are respectively captured;
a step of generating, on the basis of image data of the captured plurality of projected images, an oblique image which is a two-dimensional tomographic image along a plane intersecting a detection surface of the X-ray detection unit;
a step of acquiring information on the range irradiation angles of the X-ray generation unit relative to the X-ray detection unit when each of the plurality of projected images is captured; and a step of controlling whether or not to execute the step for generating the oblique image in accordance with the information on the range of irradiation angles of the X-ray generation unit and information about an oblique angle for generating the oblique image,
wherein the oblique angle does not exceed the range of irradiation angles.

* * * * *